(12) United States Patent
Ito et al.

(10) Patent No.: US 12,409,296 B2
(45) Date of Patent: Sep. 9, 2025

(54) SEAT DEVICE

(71) Applicant: TS TECH CO., LTD., Asaka (JP)

(72) Inventors: Takayoshi Ito, Tochigi (JP); Kensuke Mizoi, Tochigi (JP); Kohei Kowata, Tochigi (JP); Taro Murayama, Tochigi (JP); Yuki Yoshioka, Tochigi (JP); Kazuhiro Ohshima, Tochigi (JP); Akira Miyoshi, Tochigi (JP); Ryuta Kashino, Tochigi (JP); Hajime Yoshida, Tochigi (JP); Yichen Li, Tochigi (JP); Naoya Matsumoto, Tochigi (JP)

(73) Assignee: TS TECH CO., LTD., Asaka (JP)

( * ) Notice: Subject to any disclaimer, the term of this patent is extended or adjusted under 35 U.S.C. 154(b) by 276 days.

(21) Appl. No.: 17/781,609

(22) PCT Filed: Dec. 2, 2020

(86) PCT No.: PCT/JP2020/044876
§ 371 (c)(1),
(2) Date: Jun. 1, 2022

(87) PCT Pub. No.: WO2021/112129
PCT Pub. Date: Jun. 10, 2021

(65) Prior Publication Data
US 2023/0001129 A1 Jan. 5, 2023

Related U.S. Application Data

(60) Provisional application No. 62/951,623, filed on Dec. 20, 2019, provisional application No. 62/942,466, filed on Dec. 2, 2019.

(51) Int. Cl.
A47C 7/72 (2006.01)
A47C 7/74 (2006.01)
(Continued)

(52) U.S. Cl.
CPC ............ *A61M 21/02* (2013.01); *A47C 7/748* (2013.01); *A61B 5/18* (2013.01);
(Continued)

(58) Field of Classification Search
None
See application file for complete search history.

(56) References Cited

U.S. PATENT DOCUMENTS 10,433,646 B1 * 10/2019 Schmidt ................. A47C 7/748
11,818,956 B2 * 11/2023 Getman ................. A47C 7/748
(Continued)

FOREIGN PATENT DOCUMENTS

JP   H05-146343 A   6/1993
JP   H06-68752 U   9/1994
(Continued)

OTHER PUBLICATIONS

PCT International Search Report (w/ English translation) for corresponding PCT Application No. PCT/JP2020/044876, mailed on Jan. 26, 2021, 5 pages.

*Primary Examiner* — Philip F Gabler
(74) *Attorney, Agent, or Firm* — Dority & Manning, P.A.

(57) ABSTRACT

To better fulfill a sleep-inducing function for a seated person, a seat device includes a pressing device provided in a seat back and configured to press a back or a waist of a seated person to induce breathing; at least one of a temperature adjusting device configured to change a temperature of a seat cushion and/or the seat back and a shape adjusting device configured to change a surface shape of the seat cushion and/or the seat back; and a controller configured to control the pressing device to press the back or the waist of the seated person at a set cycle corresponding to a breathing (Continued)

cycle of a person at a sleeping time, and control the at least one of the temperature adjusting device and the shape adjusting device.

19 Claims, 15 Drawing Sheets

(51) Int. Cl.
  *A61B 5/18* (2006.01)
  *A61M 21/02* (2006.01)
  *A61M 21/00* (2006.01)
  *B60N 2/90* (2018.01)

(52) U.S. Cl.
  CPC ............... *A61M 2021/0022* (2013.01); *A61M 2021/0066* (2013.01); *A61M 2021/0083* (2013.01); *A61M 2021/0088* (2013.01); *B60N 2/976* (2018.02)

(56) References Cited

U.S. PATENT DOCUMENTS

| | | | | |
|---|---|---|---|---|
| 2016/0136385 | A1* | 5/2016 | Scorcioni | A61B 5/4812 600/26 |
| 2016/0325656 | A1* | 11/2016 | Ziolek | B60N 2/5685 |
| 2018/0088573 | A1* | 3/2018 | Watanabe | B60N 2/914 |
| 2018/0125256 | A1* | 5/2018 | Tsern | G05B 13/0265 |
| 2018/0206783 | A1* | 7/2018 | Yoon | A61B 5/024 |
| 2019/0073990 | A1* | 3/2019 | Moss | A61M 1/159 |
| 2020/0178887 | A1* | 6/2020 | Correa Ramírez | A61B 5/4809 |
| 2021/0169417 | A1* | 6/2021 | Burton | A61B 5/4857 |
| 2021/0257080 | A1* | 8/2021 | Iliffe-Moon | B60N 2/5621 |
| 2022/0144299 | A1* | 5/2022 | Park | B60W 40/08 |
| 2023/0137120 | A1* | 5/2023 | Kubota | A61B 5/024 5/616 |
| 2023/0166638 | A1* | 6/2023 | Kotani | B60N 2/22 701/49 |
| 2023/0173221 | A1* | 6/2023 | Shouldice | G16H 20/40 600/26 |

FOREIGN PATENT DOCUMENTS

| | | | |
|---|---|---|---|
| JP | 2002119596 A | * | 4/2002 |
| JP | 2002-143251 A | | 5/2005 |
| JP | 2005-296452 A | | 10/2005 |
| JP | 2012-065728 A | | 4/2012 |
| JP | 2015-097611 A | | 5/2015 |
| JP | 2018095015 A | * | 6/2018 |
| JP | 2019-137322 A | | 8/2019 |
| KR | 102280491 B1 | * | 7/2021 |

* cited by examiner

SEAT DEVICE

CROSS REFERENCE TO RELATED APPLICATIONS

This application is the U.S. National Stage entry of International Application No. PCT/JP2020/044876 filed under the Patent Cooperation Treaty on Dec. 2, 2020, which claims priority to U.S. Provisional Patent Application No. 62/942,466 filed on Dec. 2, 2019 and U.S. Provisional Patent Application No. 62/951,623 filed on Dec. 20, 2019, all of which are incorporated herein by reference.

TECHNICAL FIELD

The present invention relates to a seat device, and more particularly, to a seat device that has a sleep-inducing function for a seated person.

BACKGROUND ART

As a seat device for a vehicle such as an automobile, a seat device having a function of inducing breathing of a seated person is known (for example, Patent Documents 1 and 2). This seat device induces the breathing of a prescribed cycle that is suitable for relaxation by applying on a prescribed cycle a stimulus such as compression or pressure to a portion of a back of the seated person that corresponds to a lumbar vertebra or a thoracic vertebra.

PRIOR ART DOCUMENT(S)

Patent Document(s)

Patent Document 1: JP2005-296452A
Patent Document 2: JP2012-65728A

SUMMARY OF THE INVENTION

Task to be Accomplished by the Invention

To enable a person traveling by a vehicle such as an automobile, an aircraft, and a ship to recover from a lack of sleep, it is useful to make an improvement for inducing sleep of the person seated on a seat device and letting the person sleep comfortably.

In an automobile having an autonomous driving function that is being developed in recent years, the driver can sleep while driving the automobile. Accordingly, a seat device that fulfills a sleep-inducing function for the seated person becomes more useful for a driver's seat.

For these reasons, there is an increasing demand for the development of the seat device that can better fulfill a sleep-inducing function for the seated person.

In view of the above background, an object of the present invention is to provide a seat device that can better fulfill a sleep-inducing function for a seated person.

Means for Accomplishing the Task

To achieve such an object, one aspect of the present invention provides a seat device, comprising: a seat body (35) including a seat cushion (30) and a seat back (32); a pressing device (40, 42) provided in the seat back and configured to press a back or a waist of a seated person so as to induce breathing thereof; at least one of a temperature adjusting device (52) and a shape adjusting device (44), the temperature adjusting device configured to change a temperature of the seat cushion and/or the seat back, the shape adjusting device configured to change a surface shape of the seat cushion and/or the seat back; and a controller (100) configured to control the pressing device such that the pressing device presses the back or the waist of the seated person at a set cycle corresponding to a breathing cycle of a person at a sleeping time, and control the at least one of the temperature adjusting device and the shape adjusting device.

According to this aspect, it is possible to better fulfill a sleep-inducing function for the seated person.

In the above aspect, preferably, the controller is configured to correct the set cycle upon learning the breathing cycle of the seated person at the sleeping time.

According to this aspect, it is possible to properly induce sleep by inducing breathing.

In the above aspect, preferably, the controller is configured to determine whether the breathing of the seated person is abdominal breathing or thoracic breathing, and control the pressing device so as to induce the breathing corresponding to a determination result thereof.

According to this aspect, it is possible to properly induce the breathing regardless of whether the breathing of the seated person is the abdominal breathing or the thoracic breathing.

In the above aspect, preferably, the controller is configured to control the pressing device so as to induce abdominal breathing when sleep is induced, and induce thoracic breathing when the sleep ends.

According to this aspect, when sleep is induced, it is possible to induce the breathing suitable for inducing sleep. On the other hand, when sleep ends, that is, when the seated person wakes up, it is possible to induce the breathing suitable for waking up the seated person.

In the above aspect, preferably, the seat device further comprises a breathing detecting device (72) configured to detect the breathing of the seated person, wherein in a case where the breathing detected by the breathing detecting device is unstable, the controller controls the pressing device so as to induce the breathing that eliminates unstableness in the breathing.

According to this aspect, it is possible to promote the elimination of the unstableness in the breathing of the seated person.

In the above aspect, preferably, the controller is configured to determine based on external information whether the seated person is likely to sleep, and turn on the pressing device and perform control to cause the temperature adjusting device to warm the seat cushion and the seat back upon determining that the seated person is likely to sleep.

According to this aspect, when the seated person is likely to sleep, it is possible to better induce sleep of the seated person by inducing the breathing suitable for inducing sleep and warming the seat cushion and the seat back.

In the above aspect, preferably, the seat device further comprises a warm air device (58) configured to warm feet of the seated person, wherein the controller is configured to determine based on external information whether the seated person is likely to sleep, and perform control to turn on the pressing device and the warm air device upon determining that the seated person is likely to sleep.

According to this aspect, when the seated person is likely to sleep, it is possible to better induce sleep of the seated person by inducing the breathing suitable for inducing sleep and warming the feet of the seated person.

In the above aspect, preferably, the controller is configured to control the temperature adjusting device such that temperatures of the seat cushion and the seat back rise and fall repeatedly.

According to this aspect, it is possible to relax the muscle of the seated person and thus cause a relaxing effect on the seated person.

In the above aspect, preferably, the controller is configured to determine, based on external information, whether the seated person is likely to sleep, and turn on the pressing device and control the shape adjusting device such that a massage synchronized with a breathing rhythm of the seated person is given upon determining that the seated person is likely to sleep.

According to this aspect, when the seated person is likely to sleep, it is possible to better induce sleep of the seated person by inducing the breathing suitable for inducing sleep and massaging the seated person.

In the above aspect, preferably, when the seated person is likely to sleep, the controller is configured to control the temperature adjusting device such that temperatures of the seat cushion and the seat back rise.

According to this aspect, it is possible to improve a massaging effect when the seated person is likely to sleep.

In the above aspect, preferably, the controller is configured to control the shape adjusting device such that a massage synchronized with a breathing rhythm of the seated person is given.

According to this aspect, it is possible to have a preferable massaging effect.

In the above aspect, preferably, the seat device further comprises a body pressure detecting device (46) configured to individually detect a body pressure of the seated person in each portion of the seat cushion and the seat back, wherein the controller is configured to control the shape adjusting device such that a difference in the body pressure in each portion is reduced.

According to this aspect, it is possible to distribute the body pressure and thus reduce the fatigue of the seated person seated for a long time.

In the above aspect, preferably, the controller is configured to control the shape adjusting device such that surfaces of the seat cushion and the seat back are deformed so as to prompt the seated person to change a posture.

According to this aspect, it is possible to prompt the seated person to roll over.

In the above aspect, preferably, the controller is configured to control the shape adjusting device such that surfaces of the seat cushion and the seat back are deformed at a set wake-up time so as to promote the seated person to wake up.

According to this aspect, it is possible to prompt the seated person to wake up at the wake-up time.

In the above aspect, preferably, the seat device consists of a seat device for a vehicle, more specifically, a seat device for an automobile configured to be driven autonomously.

Effect of the Invention

Thus, according to the above aspects, it is possible to provide a seat device that can better fulfill a sleep-inducing function for a seated person.

BRIEF DESCRIPTION OF THE DRAWING(S)

DETAILED DESCRIPTION OF THE INVENTION

In the following, one embodiment in which a seat device according to the present invention is applied to an automobile having an autonomous driving function will be described with reference to the drawings.

Figure 1:
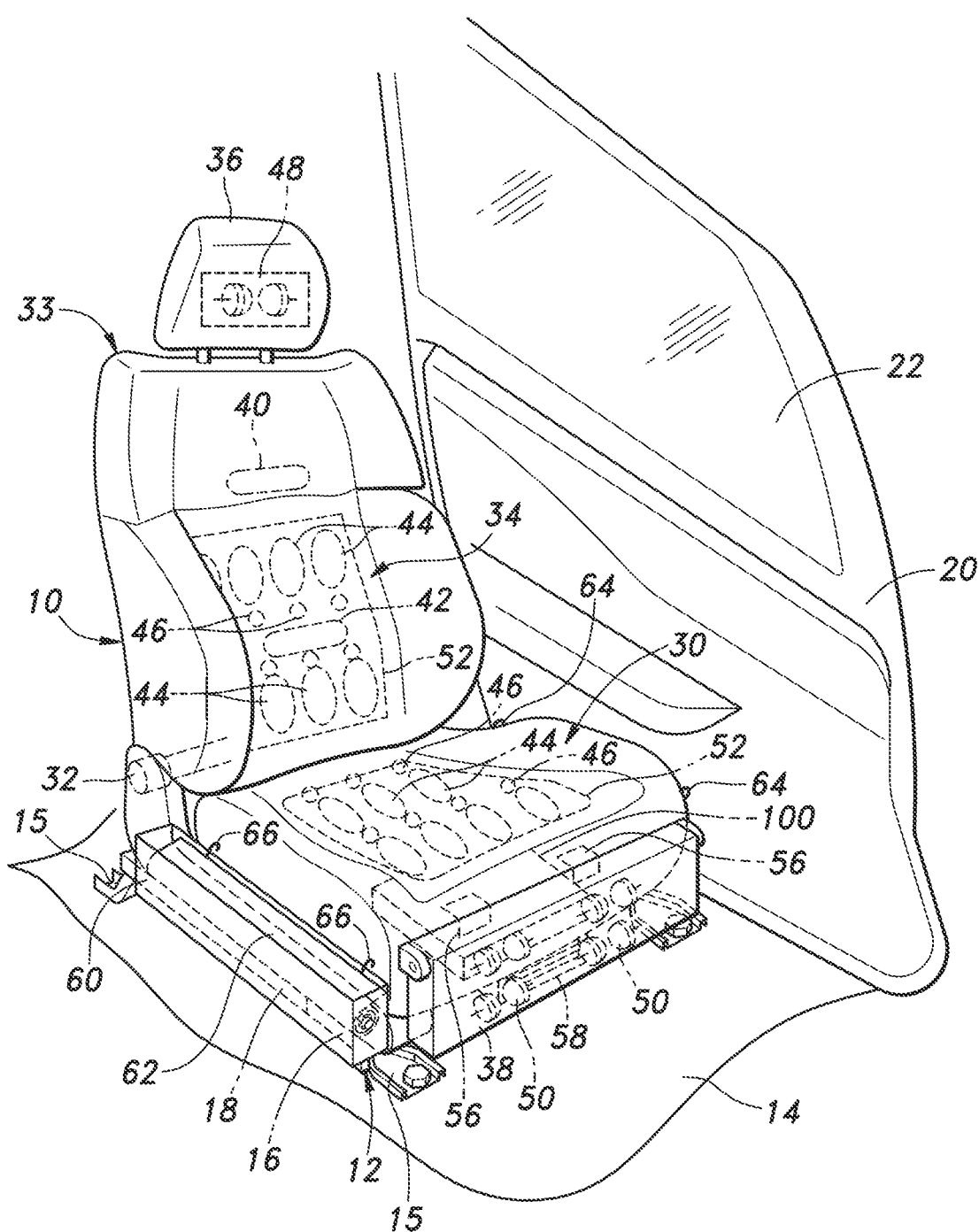
FIG. 1 is a perspective view showing a seat device according to an embodiment of the present invention.

As shown in FIG. 1, a seat device 10 according to the present embodiment is provided on a floor panel 14 of the automobile via left and right slide rail devices 12 extending in the front-and-rear direction. Each slide rail device 12 includes a lower rail 16 fixed to the floor panel 14 via brackets 15, and an upper rail 18 (upper slider) fixed to a lower surface of a seat cushion 30 and engaged with the lower rail 16 so as to slide in the front-and-rear direction.

A side door 20 is provided on a lateral side of the seat device 10. A window pane 22 is attached to an upper portion of the side door 20.

The seat device 10 includes the seat cushion 30 forming a seat surface, and a seat back 34 forming a backrest surface and connected to a rear portion of the seat cushion 30 such that the seal back 34 can be inclined by an electric reclining device 32 (hereinafter abbreviated as "reclining device"). A headrest 36 is attached to an upper portion of the seat back 34. An electric ottoman 38 (hereinafter abbreviated as "ottoman 38") is provided at a front portion of the seat cushion 30. The ottoman 38 is rotatable between a shown rotation position in which the ottoman 38 extends substantially vertically and an unshown rotation position in which the ottoman 38 extends substantially horizontally. The ottoman 38 can be fixed at any rotation position.

The seat back 34 is provided with a back pressing device 40 and a waist pressing device 42. The back pressing device 40 and the waist pressing device 42 each consist of an air pad that expands and deforms as compressed air is supplied from a compressed air source (not shown) to the air pad. The back pressing device 40 protrudes forward from a front surface of the seal back 34 thereby pressing the back (more specifically, a portion corresponding to a thoracic vertebra around a scapula) of a seated person so as to induce thoracic breathing. The waist pressing device 42 protrudes forward from the front surface of the seat back 34, thereby pressing the waist (more specifically, a portion corresponding to a lumbar vertebra) of the seated person to induce abdominal breathing.

The seat cushion 30 and the seat back 34 are each provided with seat shape adjusting devices 44 at positions excluding the back pressing device 40 and the waist pressing device 42. The seat shape adjusting devices 44 change surface shapes of the seat cushion 30 and the seat back 34. Each seat shape adjusting device 44 consists of an air pad that expands and deforms as compressed air is supplied from a compressed air source (not shown) to the air pad. Each seat shape adjusting device 44 deforms the upper surface of the seat cushion 30 upward or the front surface of the seat back 34 forward as the air pad expands and deforms.

Each seat shape adjusting device 44 massages the thigh and back of the seated person and corrects the body pressure distribution thereof by protruding the seat cushion 30 and the front surface of the seat back 34. The seat shape adjusting devices 44 are combined with each other, and thus change the surface shapes of the seat cushion 30 and the seat back 34, thereby correcting the seated posture of the seated person and prompting the seated person to roll over while sleeping. The seat shape adjusting devices 44 move with respect to each other, and thus also function as an exercise device.

The seat cushion 30 and the seat back 34 are each provided with body pressure detecting devices 46 in the vicinity of each seat shape adjusting device 44. The body pressure detecting devices 46 individually detect the body pressure of the seated person.

An electric neck massaging device 48 that massages the neck of the seated person is installed in the headrest 36. The neck massaging device 48 locally presses the neck so as to press acupoints called "Fuchi", "Tenchu", and "Kankotsu". Pressings these three acupoints is said to be effective in relieving eyestrain, a stiff shoulder, and a stiff neck, and thus has the effect of reducing fatigue of the seated person.

Electric calf massaging devices 50 that massage the calves of the seated person are installed in the ottoman 38. Each calf massaging device 50 locally presses the calf so as to press acupoints called "Shokin", "Shokan", "Shozan", "chikuhin", and "Hiyou". Pressing these five acupoints is said to be effective in reducing numbness, improving blood circulation, and relieving swelling and fatigue, and thus has the effect of reducing fatigue of the seated person.

The seat cushion 30 and the seat back 34 are provided with seat temperature adjusting devices 52 that change temperatures of the seat cushion 30 and the seat back 34. Each seat temperature adjusting device 52 consists of an electric heater for raising the temperature and a Peltier element or a cooling air supply device such as an air ventilation system (AVS) for lowering the temperature. The seat temperature adjusting devices 52 adjust surface temperatures of the seat cushion 30 and the seat back 34 within a prescribed temperature range, for example, 24° C. to 36° C. Incidentally, the ottoman 38 may also be provided with the seat temperature adjusting device 52.

On a front side of the seat cushion 30, knee back heaters 56 are provided at portions with which knee backs (backs of knees) of the seated person come into contact. Each knee back heater 56 directly warms the knee back of the seated person. A fat layer of the knee back is thin and an aorta passes through the knee back, which makes the knee back sensitive to stimuli. Accordingly, as the knee back heater 56 warms the knee back, the warmth is directly transmitted to the body, so that a thermal effect can be enhanced and fatigue can be effectively reduced.

On a lower surface of the seat cushion 30, a warm air device 58 that blows warm air toward the feet of the seated person is provided. The lower limbs including the feet are portions on which much blood of the whole body is concentrated. Accordingly, as the warm air blown by the warm air device 58 warms the feet, blood circulation can be improved, metabolism can be enhanced, oversensitivity to the cold can be relieved, and thus the health of the seated person can be improved.

A blanket box 60 is attached to a side portion of the upper rail 18 on one of left and right sides. A blanket 62 is stored in the blanket box 60. One end of the blanket 62 is fixed to the blanket box 60. The other end of the blanket 62 is provided with engagement hooks 66 configured to removably engage with locking holes 64 provided on the upper rail 18 on the other of the left and right sides.

The blanket 62 can be pulled out from the blanket box 60. The blanket 62 functions as a lap robe as a thermal member as the engagement hooks 66 engage with the locking holes 64 and thus the blanket 62 stretches over the knees of the seated person. Incidentally, the blanket 62 may extend to the chest of the seated person.

Figure 2:
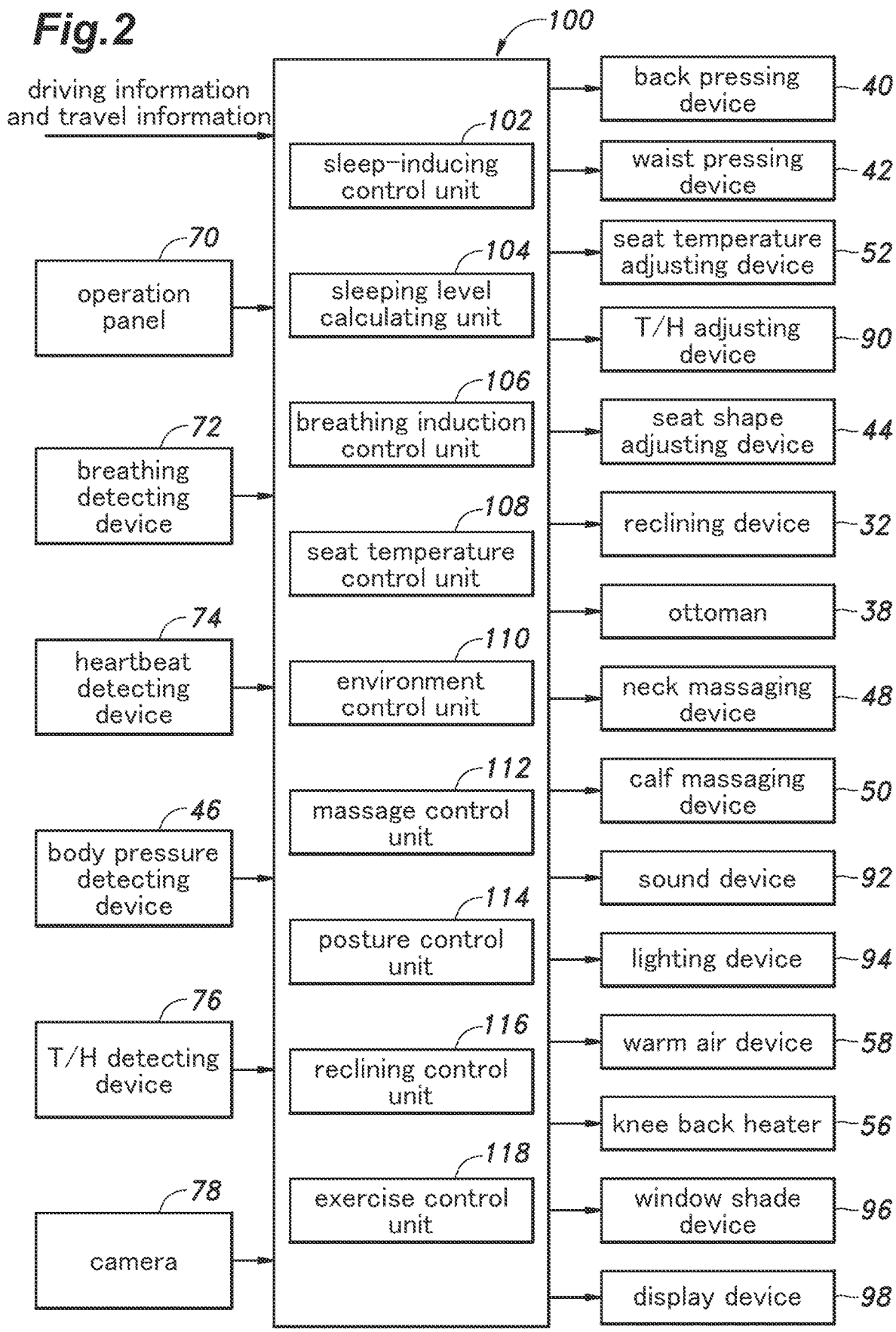
FIG. 2 is a block diagram of a control system of the seat device according to the present embodiment.

A controller 100 is provided at a lower portion of the seat cushion 30. A control system of the seat device 10 including the controller 100 will be described with reference to FIG. 2.

The controller 100 consists of an electronic information processing device including a microcomputer.

To an input side of the controller 100, an operation panel 70, a breathing detecting device 72, a heartbeat detecting device 74, each body pressure detecting device 46, a cabin temperature/humidity detecting device 76 (hereinafter abbreviated as "T/H detecting device 76"), and a camera 78 are connected. The controller 100 acquires various pieces of information from these devices.

The operation panel 70 consists of a touch panel or the like attached to a surface of a display device 98 such as a liquid crystal panel. The operation panel 70 is operated by an occupant so as to set an operation mode (automatic mode/manual mode) of the seat device 10, switch on/off various functions, and perform time settings.

The breathing detecting device 72 detects the breathing of the seated person by using the body pressure detecting devices 46, a radio wave sensor (not shown), or the like. Also, the breathing detecting device 72 detects whether the breathing of the seated person is the abdominal breathing or the thoracic breathing. The breathing detecting device 72 may acquire breathing information on the seated person by communicating with a smartwatch or wearable terminal worn by the seated person. The breathing detecting device 72 may acquire the breathing information based on the video data by the camera 78.

The heartbeat detecting device 74 acquires heartbeat information on the seated person by communicating with the smartwatch or wearable terminal worn by the seated person.

As described above, each body pressure detecting device 46 individually detects the body pressure of the seated person in each portion of the seat cushion 30 and the seat back 34. The body pressure corresponds to the load of the seated person received by the seat cushion 30 and the seat back 34.

The T/H detecting device 76 detects the temperature and humidity inside the cabin around the seat device 10.

The camera 78 captures the video for observing the behavior of the seated person.

Driving information and travel information on the automobile are input to the controller 100. The driving information on the automobile includes information on whether the automobile is driven autonomously. The travel information on the automobile includes information on travel acceleration of the automobile.

By executing a computer program, the controller 100 embodies a sleep-inducing breathing induction control unit 102 (hereinafter abbreviated as "sleep-inducing control unit 102"), a sleeping level calculating unit 104, a breathing induction control unit 106, a seat temperature control unit 108, a cabin environment control unit 110 (hereinafter abbreviated as "environment control unit 110"), a massage control unit 112, a posture control unit 114, a reclining control unit 116, and an exercise control unit 118. Accordingly, the controller 100 performs various kinds of control.

To an output side of the controller 100, the back pressing device 40, the waist pressing device 42, each seat temperature adjusting device 52, a cabin temperature/humidity adjusting device 90 (hereinafter abbreviated as "T/H adjusting device 90"), each seat shape adjusting device 44, the reclining device 32, the ottoman 38, the neck massaging device 48, the calf massaging device 50, a cabin sound device 92 (hereinafter abbreviated as "sound device 92"), a cabin lighting device 94 (hereinafter abbreviated as "lighting device 94"), a window shade device 96, each knee back heater 56, the warm air device 58, and a display device 98 are connected. The controller 100 outputs signals such as control commands to these devices.

The window shade device 96 includes a liquid crystal window shade or the like installed in the window pane 22, and makes the window pane 22 opaque by an electric operation.

The operation panel 70 and the display device 98 are arranged in front of the seat device 10 (for example, arranged in an instrument panel of the automobile) so as to be operated and seen by the seated person. The display device 98 displays a setting state and operation state of each operation of the seat device 10. The setting state and operation state of each operation of the seat device 10 may be displayed on the smartwatch or wearable terminal of the seated person by using wireless communication.

The sleep-inducing control unit 102 and the breathing induction control unit 106 control the back pressing device 40 and the waist pressing device 42. The seat temperature control unit 108 controls the seat temperature adjusting device 52 and the knee back heater 56. The environment control unit 110 controls the T/H adjusting device 90, the sound device 92, the lighting device 94, and the warm air device 58. The massage control unit 112 controls the seat shape adjusting device 44, the neck massaging device 48, and the calf massaging device 50. The posture control unit 114 controls the seat shape adjusting device 44. The reclining control unit 116 controls the reclining device 32 and the ottoman 38. The exercise control unit 118 controls the seat shape adjusting device 44.

Next, each unit of the control system of the seat device 10 will be described in detail.

When the operation mode of the seat device 10 set via the operation panel 70 is the automatic mode, the sleep-inducing control unit 102 is automatically activated as it is determined (detected) that the seated person is likely to sleep based on the information acquired by the breathing detecting device 72, the heartbeat detecting device 74, and the camera 78. When the operation mode of the seat device 10 set via the operation panel 70 is the manual mode, the sleep-inducing control unit 102 is activated as a sleep induction mode is turned on according to an operation on the operation panel 70 by the occupant. In a case where the seat device 10 consists of the driver's seat, in any operation mode, the sleep-inducing control unit 102 can start only when the automobile is driven autonomously. In other words, in a case where the seat device 10 consists of the driver's seat, the sleep-inducing control unit 102 is prohibited from starting when the automobile is not driven autonomously.

When turned on, the sleep-inducing control unit 102 controls the back pressing device 40 and the waist pressing device 42 such that the back pressing device 40 and the waist pressing device 42 press the back of the seated person at a set cycle (hereinafter referred to as "control target cycle") corresponding to a breathing cycle of the seated person at a sleeping time. This control induces the breathing suitable for sleep induction.

The sleep-inducing control unit 102 sots a default value of the control target cycle to a normal breathing cycle of a human at the sleeping time or at the time of the sleep induction. The sleep-inducing control unit 102 may modify the control target cycle upon learning the breathing cycle of the seated person detected by the breathing detecting device 72. Accordingly, it is possible to properly induce sleep by inducing the breathing.

The sleep-inducing control unit 102 determines whether the breathing of the seated person is the abdominal breathing or the thoracic breathing based on the information from the breathing detecting device 72 and the camera 78. The sleep-inducing control unit 102 may perform control such that only one of the back pressing device 40 and the waist pressing device 42 operates so as to induce the breathing corresponding to a determination result thereof.

Deep breathing according to the abdominal breathing makes the parasympathetic nerve dominant, and thus relaxes the mind and body. As the abdomen swells and deflates, the blood and lymph can smoothly circulate throughout the body, so that sleep is effectively induced. The thoracic breathing makes the sympathetic nerve dominant, and thus tensions the body and wakes up the seated person. Accordingly, the waist pressing device 42 may induce the abdominal breathing when sleep is induced, while the back pressing device 40 may induce the thoracic breathing when the sleep ends (when the seated person wakes up). Accordingly, when sleep is induced, it is possible to induce the breathing suitable for inducing sleep. On the other hand, when sleep ends, it is possible to induce the breathing suitable for waking up the seated person.

The sleep-inducing control unit 102 performs control such that the operation strength of the back pressing device 40 and the waist pressing device 42 is lowered as the sleeping level calculated by the sleeping level calculating unit 104 gets higher.

As the back pressing device 40 and the waist pressing device 42 induce the breathing based on the above control, it is possible to better induce sleep and lead the seated person to sleep well.

If the breathing of the seated person is unstable, the sleep-inducing control unit 102 controls the back pressing device 40 and the waist pressing device 42 so as to induce the breathing that eliminates unstableness in the breathing. As the breathing is induced by this control, it is possible to eliminate the unstableness in the breathing of the seated person.

The sleep-inducing control unit 102 is kept on for a sleep time or nap time se by the seated person via the operation panel 70. The sleep-inducing control unit 102 is automatically turned off after the sleep time or nap time elapses. Alternatively, the sleep-inducing control unit 102 is manually turned off according to an operation on the operation panel 70 by the seated person. The sleep-inducing control unit 102 may be linked with a smartwatch or a sleep meter at home to learn a recommended mode based on a sleeping state or health state of the seated person at night, so that the sleep time or nap time can be set individually.

The sleeping level calculating unit 104 calculates the sleeping level of the seated person based on the information from the breathing detecting device 72, the heartbeat detecting device 74, the body pressure detecting device 46, the camera 78, and the like. Accordingly, it is possible to determine REM sleep and non-REM sleep relating to the depth of sleep.

When the sleep-inducing control unit 102 is turned on, the seat temperature control unit 108, the environment control unit 10, the massage control unit 112, the posture control unit 114, and the reclining control unit 116 are turned on in a sleep-inducing mode so as to better induce sleep and lead the seated person to sleep well by the synergistic effect of these units and sleep-inducing breathing induction.

In the sleep-inducing mode, that is, when the seated person is likely to sleep, the seat temperature control unit 108 slowly warms the seat surface so as to induce sleep of the seated person. When the sleeping level calculating unit 104 or the like determines that the seated person has fallen asleep, the seat temperature control unit 108 controls the seat temperature adjusting device 52 such that the seat temperature gets lower than the time before sleep. Hereinafter, the adjustment of the seat temperature by this control will be referred to as "sleep-inducing seat temperature adjustment".

Accordingly, it is possible to cause the effect of leading the seated person to sleep well according to the sleep-inducing breathing induction by the back pressing device 40 and the waist pressing device 42 and the sleep-inducing seat temperature adjustment.

The environment control unit 110 refers to the cabin temperature/humidity detected by the T/H detecting device 76, thereby controlling the T/H adjusting device 90 such that the cabin temperature and cabin humidity suitable for sleep are maintained in the sleep-inducing mode. For example, the environment control unit 110 controls the T/H adjusting device 90 such that the cabin temperature rises and the cabin humidity falls when the cabin is cooled, and the cabin temperature falls and the cabin humidity rises when the cabin is warmed.

In the sleep-inducing mode (when the seated person is likely to sleep), the environment control unit 110 controls the sound device 92 such that the sound device 92 makes a sound with a rhythm suitable for the sleep induction and synchronized with the sleep-inducing breathing induction by the back pressing device 40 and the waist pressing device 42, music with a rhythm that induces sleep, or quiet music suitable for inducing sleep.

In the sleep-inducing mode (when the seated person is likely to sleep), the environment control unit 110 controls the lighting device 94 and the window shade device 96 such that an inside of the cabin becomes dark and invisible from the outside.

In the sleep-inducing mode (when the seated person is likely to sleep), the environment control unit 110 controls the warm air device 58 such that the warm air flows at the feet of the seated person.

By the above control, a cabin environment (sleep-inducing environment) in which the seated person can easily sleep is organized. Accordingly, it is possible to cause the effect of leading the seated person to sleep by the sleep-inducing breathing induction by the back pressing device 40 and the waist pressing device 42 and the setting of the sleep-inducing environment.

The environment control unit 110 can also perform control to change the brightness of the lighting device 94 and the sound of the sound device 92 according to the breathing rhythm of the seated person. This control makes it easier for the sealed person to be aware of his/her breathing, and thus it is possible to cause the effect of yoga or meditation.

In the sleep-inducing mode (when the seated person is likely to sleep), the massage control unit 112 controls the seat shape adjusting device 44, the neck massaging device 48 and the calf massaging device 50 to give a massage (sleep-inducing massage) suitable for the sleep induction and synchronized with the sleep-inducing breathing induction by the back pressing device 40 and the waist pressing device 42. Accordingly, it is possible to cause the effect of leading the seated person to sleep well by the sleep-inducing breathing induction by the back pressing device 40 and the waist pressing device 42 and the sleep-inducing massage.

In the sleep-inducing mode (when the seated person is likely to sleep), the posture control unit 114 controls the seat shape adjusting device 44 based on the body pressure distribution or the like detected by each body pressure detecting device 46 so as to correct the body pressure distribution, prevent bedsores, and prompt the seated person to roll over. In other words, the posture control unit 114 controls the seat shape adjusting device 44 such that a difference in the body pressure in each portion of the seat cushion 30 and the seat back 34 is reduced or the surfaces of the seat cushion 30 and the seat back 34 are deformed so as to prompt the seated person to change a posture.

Accordingly, it is possible to cause the effect of leading the seated person to sleep well by performing the sleep-inducing breathing induction by the back pressing device 40 and the waist pressing device 42, preventing bedsores, and prompting the seated person to roll over.

In a case where the seated person sleeps while the automobile is traveling, the posture control unit 114 performs control such that the seat shape adjusting device 44 causes the seat cushion 30 and the seat back 34 to hold the seated person tight or hardens the seat cushion 30 and the seat back 34 according to the travel acceleration. Accordingly, it is possible to prevent the body of the seated person at the sleeping time from moving significantly due to the travel acceleration, and thus cause the effect of keeping stable sleep.

In the sleep-inducing mode (when the seated person is likely to sleep), the reclining control unit 116 controls the reclining device 32 and the ottoman 38 so as to make the seat device 10 completely flat or nearly flat. Thus, the seated person can take a posture in which sleep is likely to be induced, so that the seated person can sleep well. Accordingly, it is possible to cause the effect of better inducing sleep and cause the seated person to sleep well by the above posture and the sleep-inducing breathing induction by the back pressing device 40 and the waist pressing device 42.

Due to the above functions and effects, the seated person is less likely to become uncomfortable at the sleeping time, and can sleep comfortably for a long time. Further, the seated person can be prevented from waking up earlier than the scheduled time when taking a nap.

At the end of the sleep-inducing mode, the posture control unit 114 and the reclining control unit 116 perform, as a wake-up process, control to cause the seat shape adjusting device 44 to operate rapidly or vibrate, or to erect the seat back 34 by the reclining device 32. This control prompts the sleeping seated person to wake up.

If sleeping deeply at the time of short sleep such as a nap, the seated person may feel tired after waking up. As such, the sleeping level calculating unit 104 calculates the sleeping level. At the time of short sleep, the sleeping level calculating unit 104 may prompt the seated person to wake up at the stage where the sleeping level is low. At the time of long sleep, the sleeping level calculating unit 104 may prompt the seated person to wake up when the sleeping level is low (when REM sleep is caused). The seated person may be prompted to wake up as the seat shape adjusting device 44 operates rapidly or vibrates, the reclining device 32 erects the seat back 34, the sound device 92 outputs a sound suitable for waking up the seated person, or the lighting device 94 lights the cabin suitably for waking up the seated occupant.

Deep breathing according to the abdominal breathing makes the parasympathetic nerve dominant, and thus relaxes the mind and body. As the abdomen swells and deflates, the blood and lymph can smoothly circulate throughout the body, so that sleep is effectively induced. The thoracic breathing makes the sympathetic nerve dominant, and thus tensions the body and wakes up the seated person. Accordingly, the waist pressing device 42 may induce the abdominal breathing when sleep is induced, while the back pressing device 40 may induce the thoracic breathing when the sleep ends (when the seated person wakes up).

The display device 98, the smartphone of the seated person, or the tablet terminal of the seated person may display whether the breathing of the seated person is induced properly.

The breathing induction control unit 106 is activated by the operation on the operation panel 70 by the seated person, and controls the back pressing device 40 and the waist pressing device 42 such that the breathing (the abdominal breathing or the thoracic breathing) of the seated person determined by the breathing detecting device 72 is induced. Accordingly, the breathing of the seated person that matches the current breathing state is induced, and thus the seated person can have a comfortable time with proper breathing. The breathing state of the seated person is displayed on the display device 98.

The breathing induction control unit 106 determines whether the seated person is excited based on the information from the breathing detecting device 72, the heartbeat detecting device 74, and the camera 78. When the seated person is excited, the breathing induction control unit 106 controls the back pressing device 40 such that the thoracic breathing is induced. Accordingly, it is possible to prompt the seated person to calm down by breathing.

The seat temperature control unit 108 is activated in a relaxing mode as the operation panel 70 is operated by the seated person. In the relaxing mode, the seat temperature control unit 108 controls the seat temperature adjusting device 52 such that the surface temperatures of the seat cushion 30 and the seat back 34 rise and fall repeatedly in a prescribed cycle. Accordingly, it is possible to relax the muscle of the seated person and thus cause a relaxing effect on the seated person.

In this relaxing mode, the knee back heater 56 directly warms the knee back of the seated person and the warm air from the warm air device 58 warms the feet of the seated person.

The massage control unit 112 is activated in the relaxing mode as the operation panel 70 is operated by the seated person. In the relaxing mode, the massage control unit 112 controls the seat shape adjusting device 44, the neck massaging device 48, and the calf massaging device 50 such that a massage to reduce the fatigue of the seated person is given. This massage may be given so as to match the rhythm of the breathing detected by the breathing detecting device 72. Alternatively, this massage may be given with a rhythm that matches the timing of the breathing induction by the breathing induction control unit 106.

The massage by the seat shape adjusting device 44 may be given in a state where the seat temperature adjusting device 52 raises the surface temperatures of the seat cushion 30 and the seat back 34. Further, the massage by the seat shape adjusting device 44 may be given strongly on a portion whose body pressure detected by the body pressure detecting device 46 is high so as to actively improve the blood flow in the portion whose body pressure is high.

The seat shape adjusting device 44 can induce the breathing rhythm of the seated person by gradually slowing down the rhythm of the massage so as to prompt the seated person to breathe slowly and deeply. As the massage is given simultaneously with deep breathing, the relaxing effect can be enhanced. Further, this massage may be given at not only the seat cushion 30 and the seat back 34 but also an elbow rest (not shown) or the ottoman 38.

The posture control unit 114 is activated in the relaxing mode as the operation panel 70 is operated by the seated person. In the relaxing mode, the posture control unit 114 calculates the body pressure distribution based on the information from the body pressure detecting device 46, and controls the seat shape adjusting device 44 such that the body pressure is evenly distributed. Accordingly, the body pressure is distributed in the seat cushion 30 and the seat back 34, and thus it is possible to cause the effect of reducing the fatigue of the seated person seated for a long time.

The reclining control unit 116 is activated as the operation panel 70 is operated by the seated person, and controls the reclining device 32 according to the operation on the operation panel 70. Accordingly, a reclining state according to the request of the seated person is generated.

The exercise control unit 118 is activated as the operation panel 70 is operated by the seated person, and controls the seat shape adjusting device 44 in an exercise mode. In the exercise mode, the seat shape adjusting device 44 moves synchronously with the breathing to cause the seated person to get some exercise of moving his/her waist synchronously with the breathing.

Accordingly, the seated person gets some exercise of moving his/her waist synchronously with the breathing, so that a lack of exercise of the seated person can be effectively prevented, the health of the seated person can be effectively promoted, and a relaxing effect can be caused.

The exercise control unit 118 controls the seat shape adjusting device 44 such that the rhythm of the exercise matches the rhythm of the breathing. Accordingly, it is possible to promote efficient breathing and improve an exercise effect. An exercise level of the exercise may correspond to the breathing and heart rate of the seated person. Accordingly, the seated person can get a reasonable exercise. At the end of the exercise, deep breathing may be prompted by the waist pressing device 42 or the like. In the exercise mode, the exercise control unit 118 may also cause a stretching effect to relax the body of the seated person.

Next, the operation of the seat device 10 will be described with reference to a flowchart shown in FIG. 3. The flowchart is performed by the controller 100.

First, the controller 100 determines whether the automobile is driven autonomously (step S10). If the automobile is driven autonomously (step S10: Yes), the controller 100 determines whether the operation mode of the seat device 10 is the automatic mode (step S11).

If the operation mode is the automatic mode (step S11: Yes), the controller 100 makes a sleep-inducing determination (SI determination) (step S12). The sleep-inducing determination is a determination as to whether the seated person is likely to sleep. Upon determining based on various pieces of input information that the seated person is likely to sleep (step S12: Yes), the controller 100 executes the sleep-inducing breathing induction (SI induction) (step S13). Subsequently, the controller 100 executes the respective steps (step S14 to step S18) of sleep-inducing seat temperature adjustment (SI adjustment), sleep-inducing reclination (SI reclination), a sleep-inducing massage (SI massage), a sleep-inducing environment setting (SI setting), and posture correction until the wake-up time arrives (step S19). As the initial setting of the automatic mode, at least one of the sleep-inducing seat temperature adjustment, the sleep-inducing reclination, the sleep-inducing massage, the sleep-inducing environment setting, and the posture correction may be selected via the operation panel 70 according to the preference of the seated person or the like.

In the sleep-inducing breathing induction (step S13), the back pressing device 40 and the waist pressing device 42 apply a pressing stimulus suitable for the sleep induction to the back and waist of the seated person on a prescribed cycle. Accordingly, the breathing suitable for the sleep induction is induced.

In the sleep-inducing seat temperature adjustment (step S14) under the sleep-inducing breathing induction, the seat temperature adjusting device 52 slowly warms the surface of the seat to induce sleep of the seated person. When the seated person falls asleep, the seat temperature adjusting device 52 makes the seat temperature lower than the time before sleep, thereby generating a comfortable sleeping environment.

In the sleep-inducing reclination (step S15) under the sleep-inducing breathing induction, the reclining device 32 and the ottoman 38 make the seat device 10 completely flat or nearly flat, thereby generating the comfortable sleeping environment.

In the sleep-inducing massage (step S16) under the sleep-inducing breathing induction, the seat shape adjusting device 44, the neck massaging device 48, and the calf massaging device 50 give a massage synchronized with the sleep-inducing breathing induction.

In the sleep-inducing environment setting (step S17), the sound device 92 outputs a sound suitable for the sleep induction, the lighting device 94 lights the cabin suitably for the sleep induction, and the window shade device 96 shields the window pane 22 suitably for the sleep induction.

Figure 4:
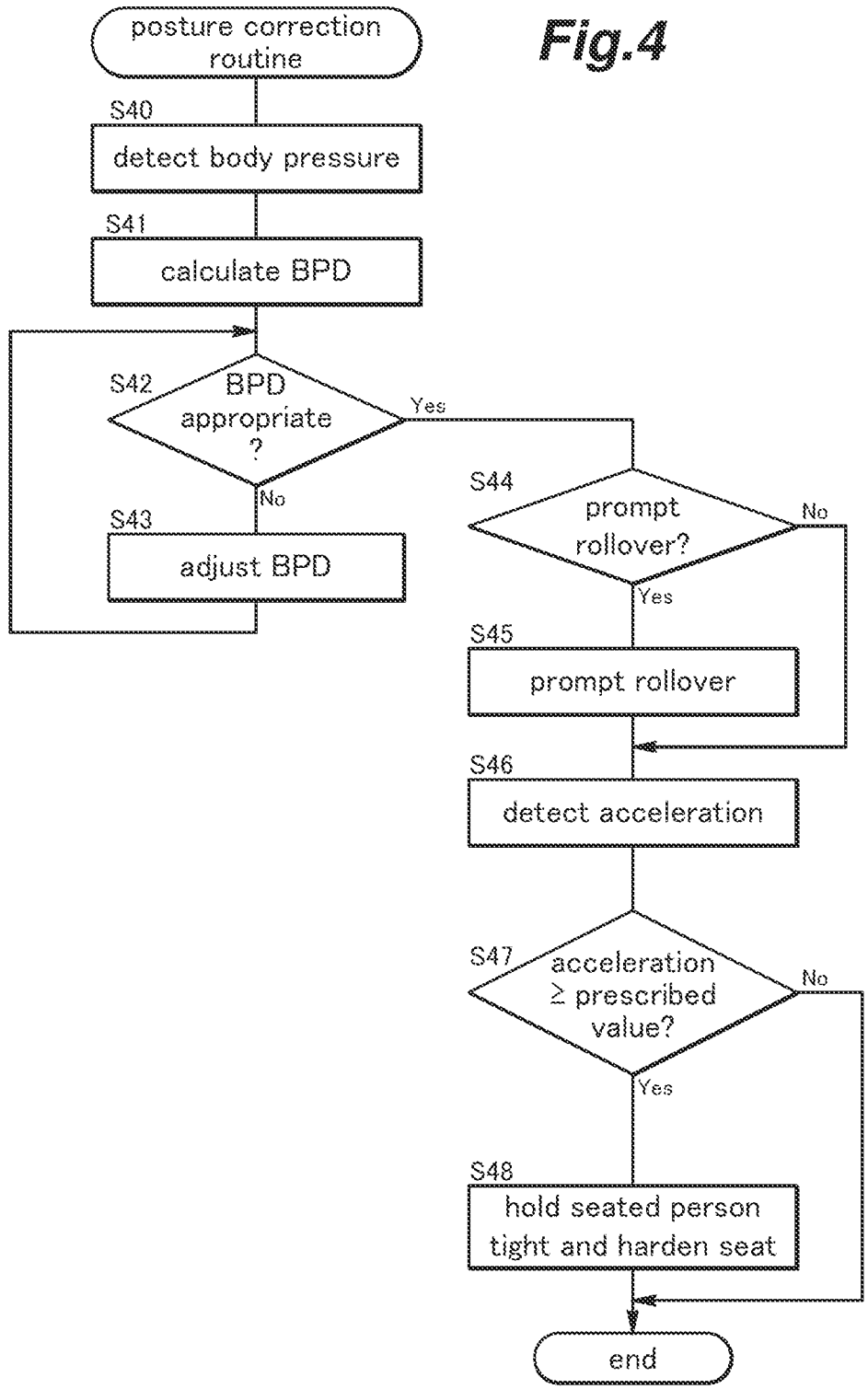
FIG. 4 is a flowchart of a posture correction routine of the seat device according to the present embodiment.

In the posture correction (step S18), a posture correction routine shown in FIG. 4 is performed.

The posture correction routine shown in FIG. 4 will be described.

First, each body pressure detecting device 46 detects the body pressure in each portion of the seat cushion 30 and the seat back 34, thereby acquiring the body pressure information (step S40). Next, the controller 100 calculates the body pressure distribution (BPD) in the seat cushion 30 and the seat back 34 based on the body pressure information on each portion (step S41), and determines whether the body pressure distribution is appropriate (step S42). One of the conditions for the body pressure distribution to be appropriate is that there is no portion where the body pressure is locally higher than the other portions.

If the body pressure distribution is not appropriate (step S42: No), the seat shape adjusting device 44 performs a correction process for adjusting the body pressure distribution (step S43).

If the body pressure distribution is appropriate (step S42: Yes), the controller 100 determines whether to prompt the seated person to roll over (step S44). Determination as to whether to prompt the seated person to roll over is made based on the breathing, heartbeat, video data of the seated person, and the like. Upon determining to prompt the seated person to roll over (step S44: Yes), the seat shape adjusting device 44 changes the surface shapes of the seat cushion 30 and the seat back 34 into a shape that prompts the seated person to roll over or a shape that makes it easy for the seated person to roll over (step S45).

Next, the travel acceleration (hereinafter abbreviated as "acceleration") of the automobile is detected (step S46), and the controller 100 determines whether the acceleration is equal to or greater than a prescribed value (step S47). When the acceleration is equal to or greater than the prescribed value (step S47: Yes), the seat shape adjusting device 44 causes the seat cushion 30 and the seat back 34 to hold the seated person tight and hardens the seat cushion 30 and the seat back 34 (step S48). Accordingly, the posture correction routine ends.

Figure 3:
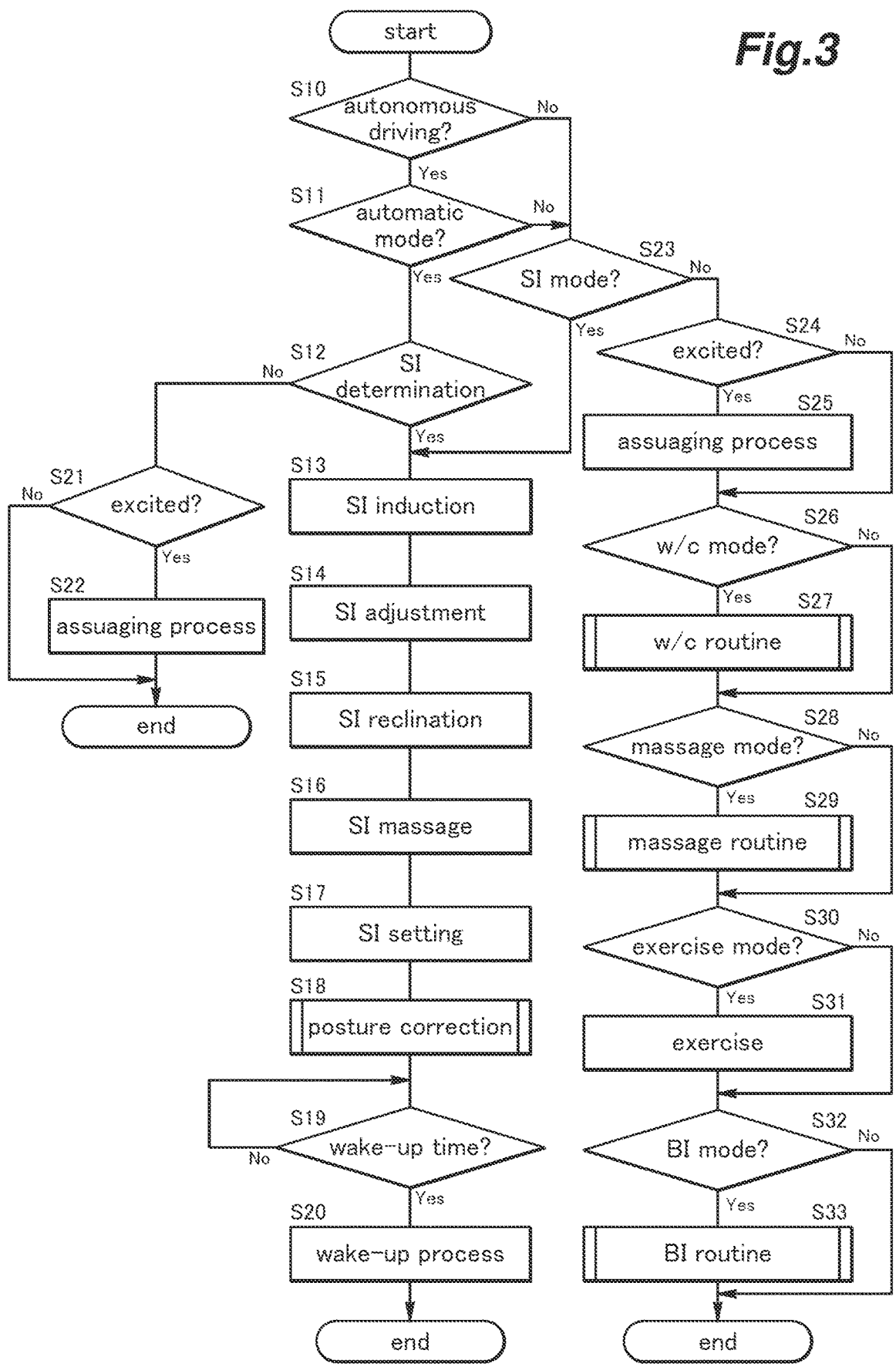
FIG. 3 is a general flowthart of the control system of the seat device according to the present embodiment.

Next, returning to the flowchart shown in FIG. 3, the controller 100 determines whether a prescribed wake-up time arrives (step S19) after the above-mentioned steps S13 to S18. When the wake-up time arrives (step S19: Yes), the controller 100 executes a wake-up process step S20).

In the sleep-inducing determination in step S12, upon determining that the seated person is not likely to sleep (step S12: No), the controller 100 determines whether the seated person is excited (step S21). This determination is made based on the change in the breathing cycle or heartbeat of the seated person, or the video data of the seated person. Upon determining that the seated person is excited (step S21: Yes), the controller 100 performs an assuaging process of the seated person, namely, a process of suppressing the excitement of the seated person (step S22). The assuaging process includes induction of the abdominal breathing by the waist pressing device 42, a massage by the seat shape adjusting device 44, the neck massaging device 48, and the calf massaging device 50 to improve relaxation.

In the determination of the driving mode of the automobile in step S10, upon determining that the automobile is not driven autonomously, that is, upon determining that the automobile is manually driven by the driver (step S10: No), the controller 100 determines whether the sleep-inducing mode (SI mode) is selected (step S23). Also, in the determination of the operation mode of the seat device 10 in step S11, upon determining that the operation mode is not the automatic mode, that is, upon determining that the operation mode is the manual mode (step S11: No), the controller 100 determines whether the sleep-inducing mode (SI mode) is selected (step S23).

When the sleep-inducing mode is selected (step S23: Yes), the controller 100 proceeds to step S13, and sequentially executes steps S13 to S20 in the same manner as the automatic mode.

In a case where the sleep-inducing mode is not selected. (step S23: No), the controller 100 determines whether the seated person is excited (step S24). This determination in step S24 is the same as the determination in step S21. Upon determining that the seated person is excited (step S24: Yes), the controller 100 executes an assuaging process of the seated person like step S22 (step S25).

Thereafter, the controller 100 determines whether a warming/cooling mode (w/c mode) is selected (step S26). When the warming/cooling mode is selected (step S26: Yes), the controller 100 executes a warming/cooling routine (w/c routine) shown in FIG. 5 (S27).

Figure 5:
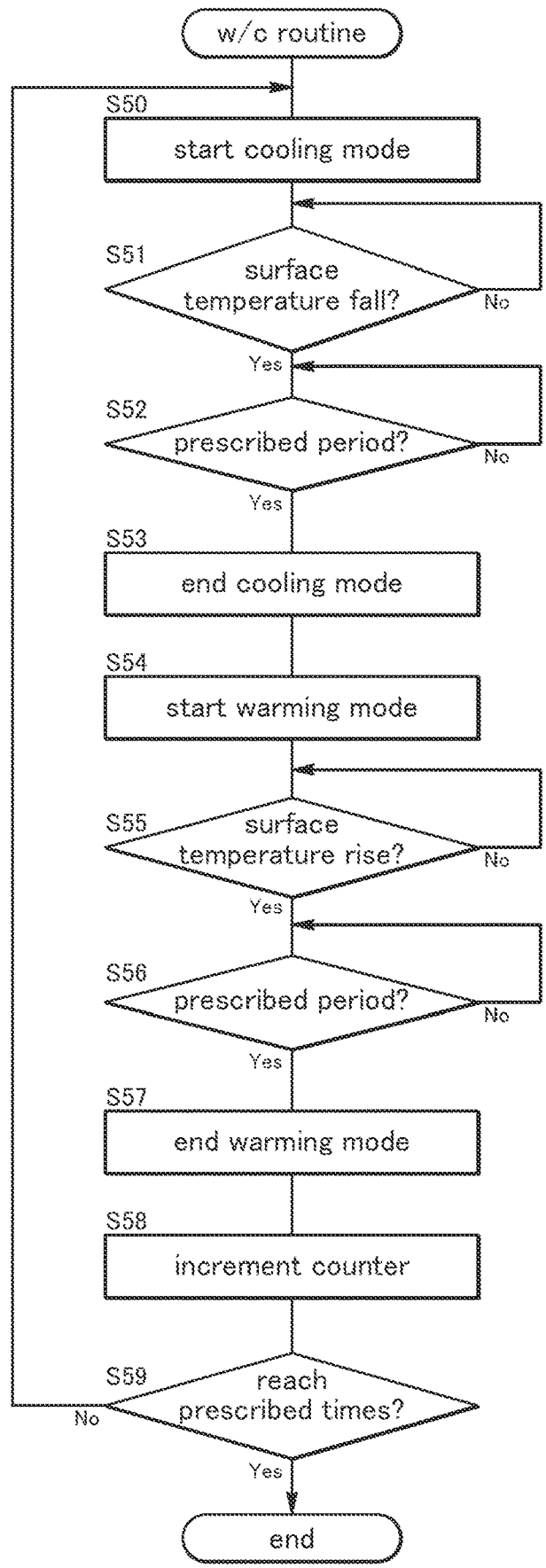
FIG. 5 is a flowchart of a warming/cooling routine of the seat device according to the present embodiment.

The warming/cooling routine (w/c routine) shown in FIG. 5 will be described.

First, the controller 100 starts a cooling mode by the Peltier element or the like of the seat temperature adjusting device 52 (step S50), and monitors whether the surface temperature of the seat (the seat cushion 30 and the seat back 34) has fallen to a prescribed value (step S51). When the surface temperature of the seat has fallen to the prescribed value (step S51: Yes), the controller 100 maintains this temperature state for a prescribed period (step S52).

When the prescribed temperature state is maintained for the prescribed period, the controller 100 ends the cooling mode (step S53), starts a warming mode by the heater of the seat temperature adjusting device 52 (step S54), and monitors whether the surface temperature of the seat has risen to a prescribed value (step S55). When the surface temperature of the seat has risen to the prescribed value (step S55: Yes), the controller 100 maintains this temperature state for a prescribed period (step S56). When the prescribed temperature state is maintained for the prescribed period, the controller 100 ends the warming mode (step S57), and increments the counter of the number of times (step S58).

The controller 100 repeatedly executes steps S50 to S58 until reaching prescribed times. Upon reaching the prescribed times (step S59: Yes), the controller 100 ends the warming cooling routine.

Next, returning to the flowchart shown in FIG. 3, the controller 100 determines whether a massage mode is selected (step S28). When the massage mode is selected (step S28: Yes), the controller 100 performs a massage routine shown in FIG. 6 (S29).

Figure 6:
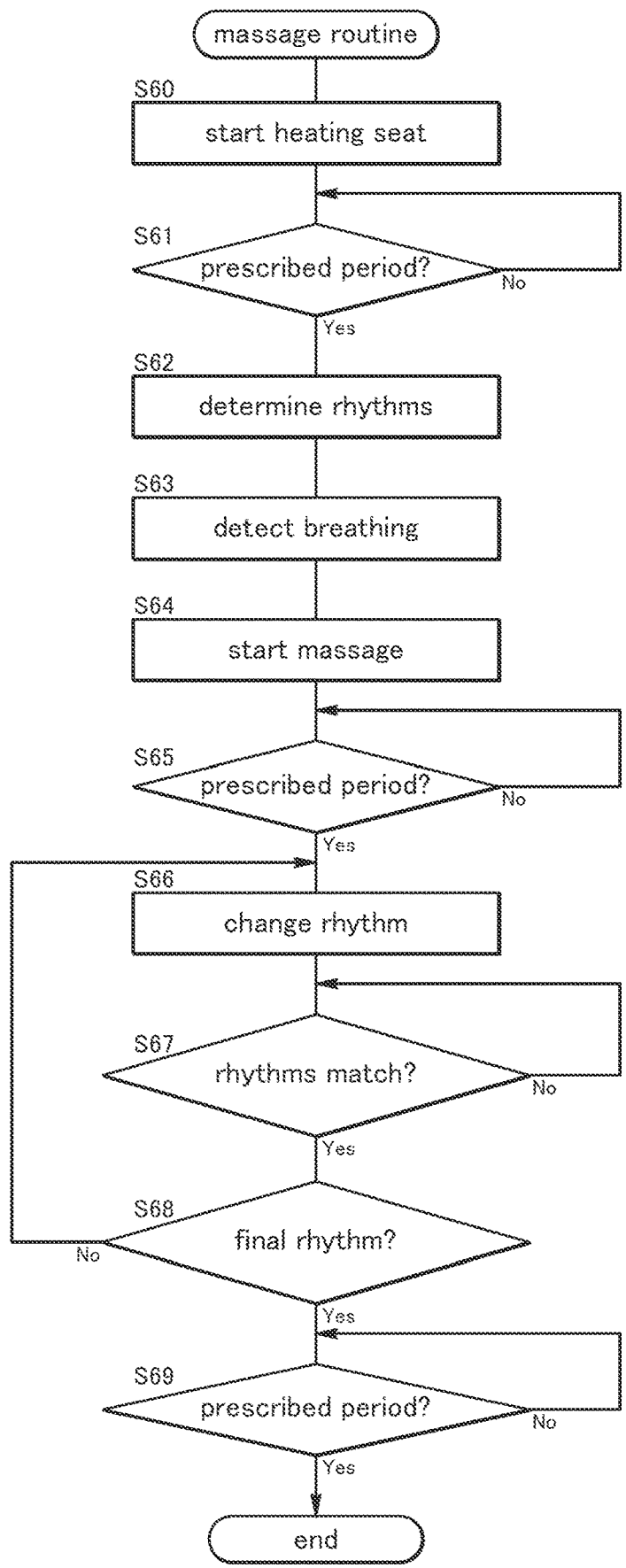
FIG. 6 is a flowchart of a massage routine of the seal device according to the present embodiment.

The massage routine shown in FIG. 6 will be described.

First, prior to the massage, the heater of the seat temperature adjusting device 52 starts heating the seat to raise the surface temperature thereof (step S60). The controller 100 monitors whether a prescribed temperature is maintained for a prescribed period (step S61). When the prescribed temperature is maintained for the prescribed period (step S61: Yes), the controller 100 determines an initial rhythm and final rhythm of the massage (step S62). The initial rhythm and final rhythm of the massage may be determined by the seated person according to the degree of the massage desired by the seated person.

Next, in a state where the breathing of the seated person is detected (step S63), the seat shape adjusting device 44 starts the massage with the initial rhythm (step S64). If a prescribed period elapses since the start of the massage (step S65: Yes), the seat shape adjusting device 44 slowly changes the rhythm of the massage (step S66) such that the rhythm of the massage approaches the final rhythm, and the controller 100 monitors whether the rhythm of the massage matches the rhythm of the breathing (step S67).

When the rhythm of massage matches the rhythm of the breathing (step S67: Yes), the controller 100 determines whether the current massage rhythm is the final rhythm (step S68). In a case where the current massage rhythm is not the final rhythm (step S68: No), the controller 100 repeats steps S66 and S67. In a case where the current massage rhythm is the final rhythm (step S68: Yes), the seat shape adjusting device 44 maintains the final rhythm until a prescribed period elapses (step S69). After that, the controller 100 ends the massage routine.

Next, returning to the flowchart shown in FIG. 3, the controller 100 determines whether the exercise mode is selected (step S30). When the exercise mode is selected (step S30: Yes), the seat shape adjusting device 44 causes the seated person to exercise (step S31).

Next, the controller 100 determines whether a breathing induction mode (BI mode) is selected (step S32). In a case where the breathing induction mode is selected (step S32: Yes), the controller 100 performs a breathing induction routine (BI routine) shown in FIG. 7 (S33).

Figure 7:
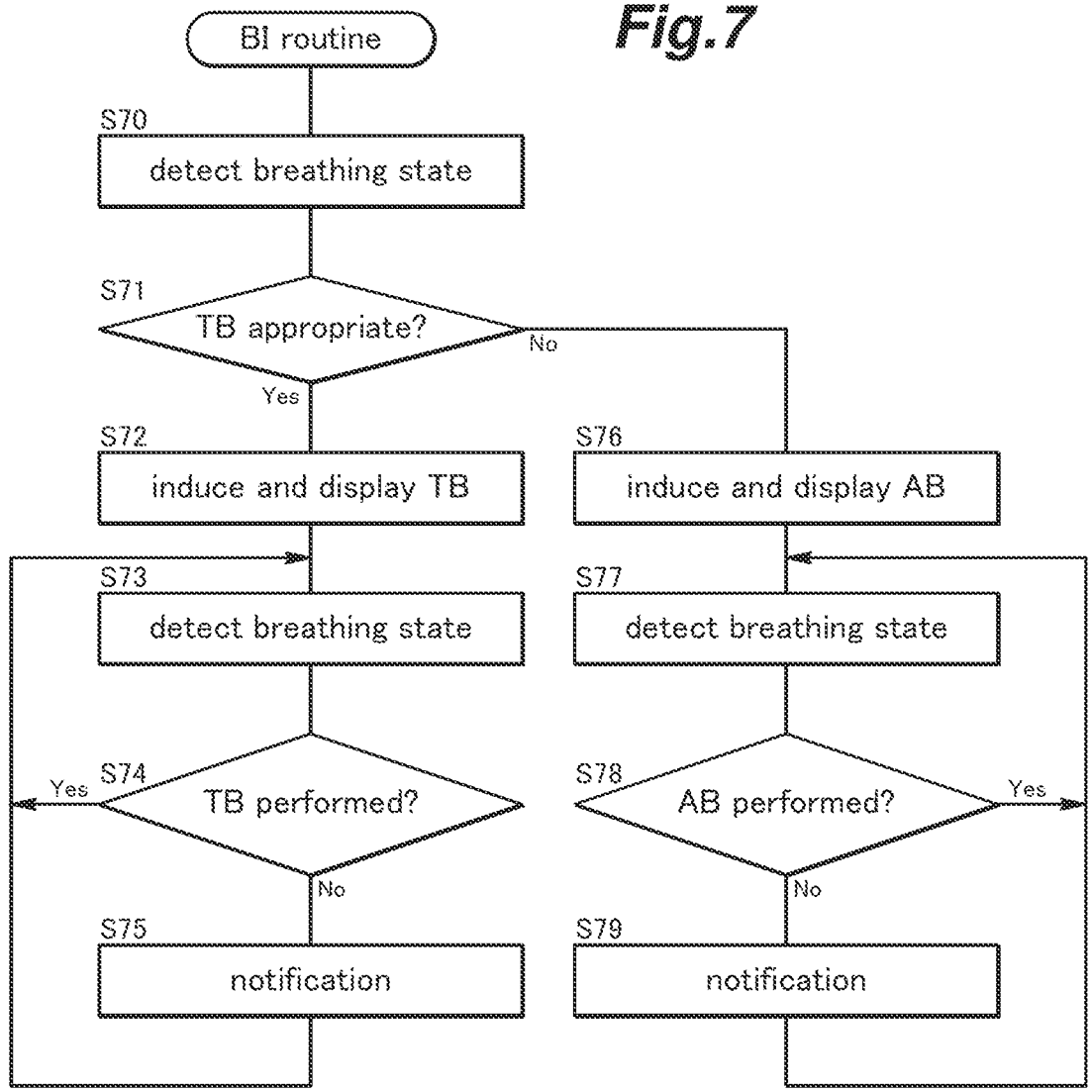
FIG. 7 is a flowchart of a breathing induction routine of the seat device according to the present embodiment.

The breathing induction routine (BI routine) shown in FIG. 7 will be described.

First, the current breathing state is detected (step S70), and the controller 100 determines whether the thoracic breathing (TB) is appropriate based on the current breathing condition (step S71). In a case where the thoracic breathing is appropriate (step S71: Yes), the back pressing device 40 induces the thoracic breathing and the fact that the thoracic breathing is induced is displayed (step S72). After that, the current breathing state is detected (step S73), and the controller 100 determines whether the thoracic breathing is performed (step S74). In a case where the thoracic breathing is performed (step S74: Yes), the controller 100 returns to step S73. In a case where the thoracic breathing is not performed (step S74: No), the controller 100 notifies the seated person that the thoracic breathing is not performed appropriately (step S75), and returns to step S73.

In the determination of step S71, in a case where the controller 100 determines that the thoracic breathing is not appropriate (step S71: No), that is, in a case where the controller 100 determines that the abdominal breathing (AB) is appropriate, the waist pressing device 42 induces the abdominal breathing and the fact that the abdominal breathing is induced is displayed (step S76). After that, the current breathing state is detected (step S77), and the controller 100 determines whether the abdominal breathing is performed (step S78). In a case where the abdominal breathing is performed (step S78: Yes), the controller 100 returns to step S77. In a case where the abdominal breathing is not performed (step S78: No), the controller 100 notifies the seated person that the abdominal breathing is not performed appropriately (step S79), and returns to step S77. When the selection of the breathing induction mode is canceled, the breathing induction routine ends.

Figure 8:
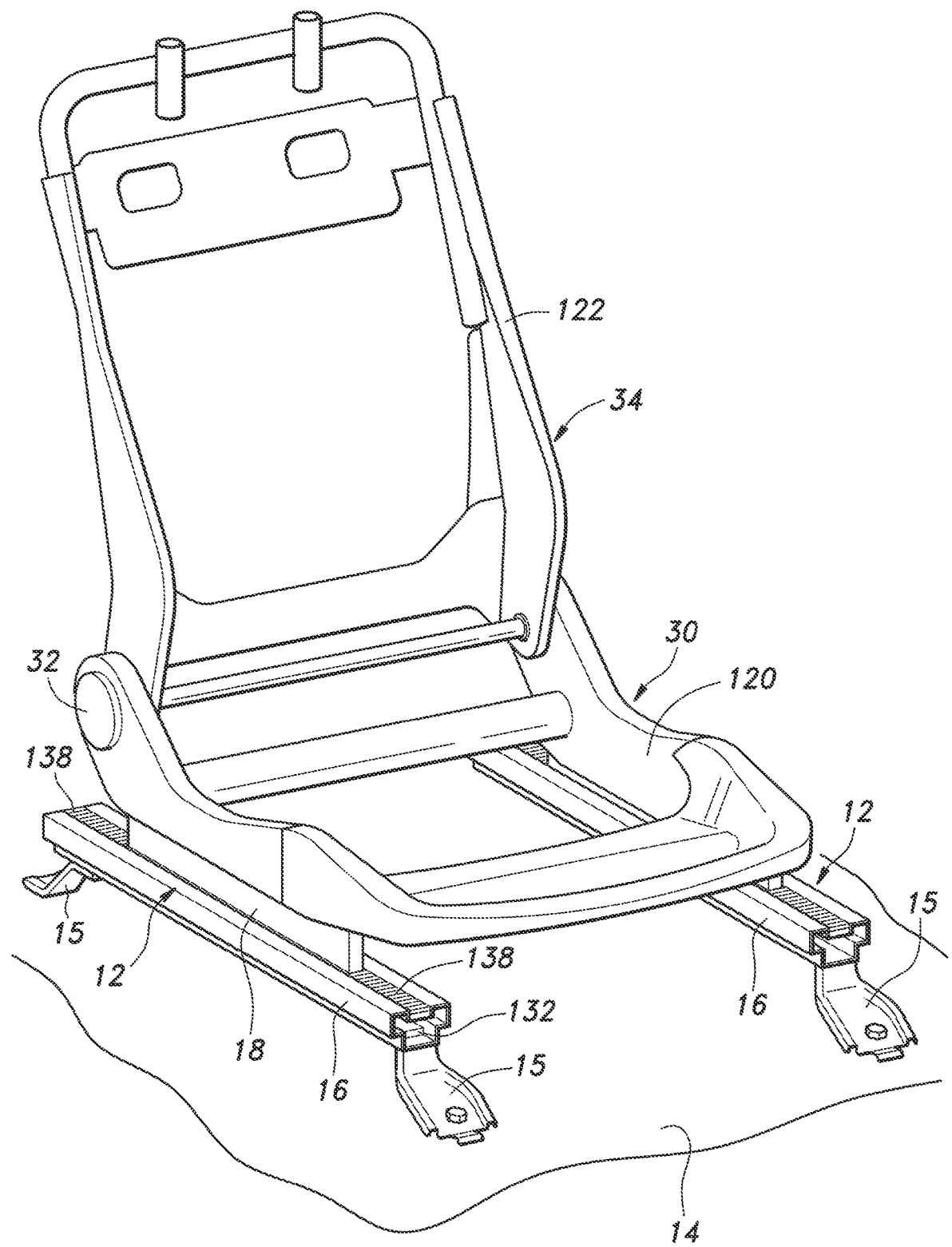
FIG. 8 is a perspective view showing a structure of the seat device according to the present embodiment.
Figure 9:
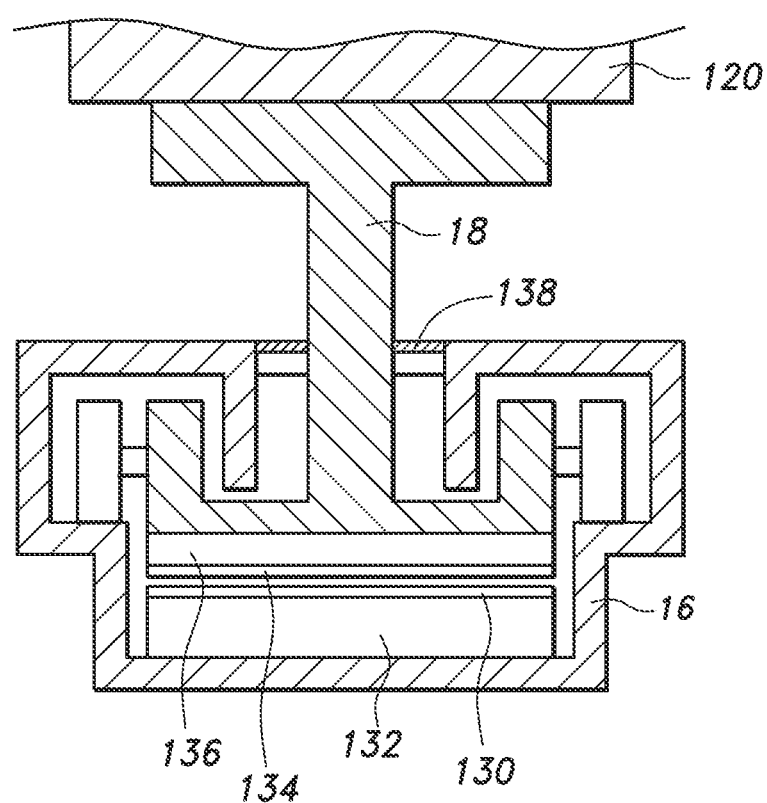
FIG. 9 is an enlarged cross-sectional view showing a main portion of a power supply mechanism of the seat device according to the present embodiment.

Next, one embodiment of a power supply mechanism that supplies electric power from a power supply (not shown) on a vehicle body side to each portion of the seat device 10 will be described with reference to FIGS. 8 and 9.

The seat cushion 30 includes a seat cushion frame 120 having a substantially square frame-like shape. The seat back 34 includes a seat back frame 122 having a substantially square frame-like shape.

A power transmitter 132 is attached to an upper surface of the lower rail 16. The power transmitter 132 includes a band-shaped power transmitting electrode 130 extending over substantially the entire length of the lower rail 16. A power receiver 136 including a power receiving electrode 134 is attached to a lower surface of the upper rail 18. The power transmitting electrode 130 and the power receiving electrode 134 face each other with a prescribed gap therebetween, and compose a non-contact type power supply mechanism using electric field coupling. Accordingly, the electric power is supplied from the power supply (not shown) on the vehicle body side to each portion of the seat device 10.

A band-shaped bellows 138 connected to the upper rail 18 is attached to the lower rail 16 so as to close an upper opening of the lower rail 16. The bellows 138 protects the power transmitting electrode 130.

Figure 10:
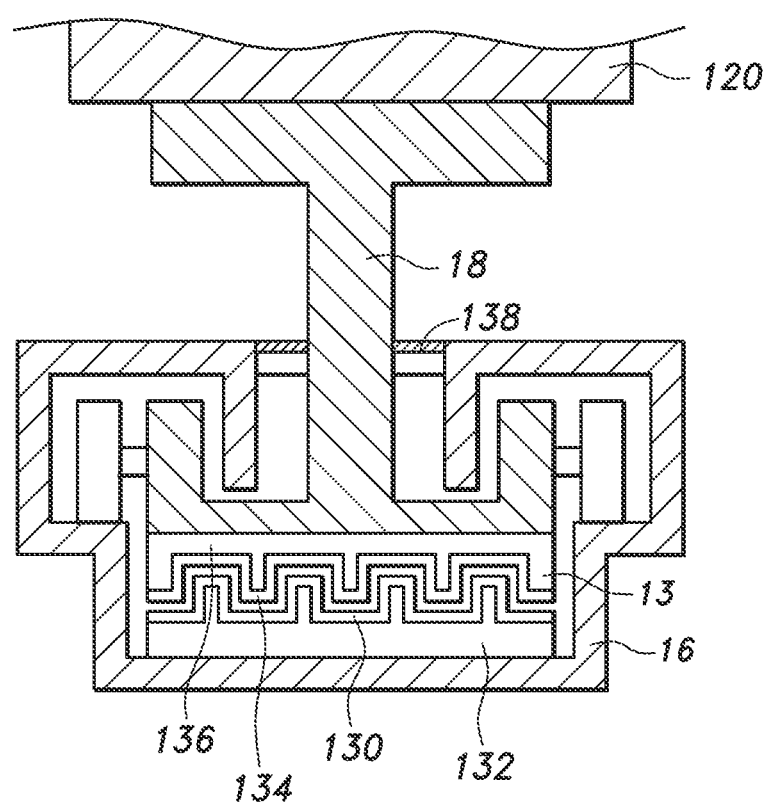
FIG. 10 is an enlarged cross-sectional view showing a main portion of a power supply mechanism of a seat device according to another embodiment.

In another embodiment, as shown in FIG. 10, the power transmitting electrode 130 and the power receiving electrode 134 have uneven surfaces that are opposed to each other so as to increase opposed areas of the power transmitting electrode 130 and the power receiving electrode 134. As the opposed areas increase, the transmittable electric power increases.

Figure 11:
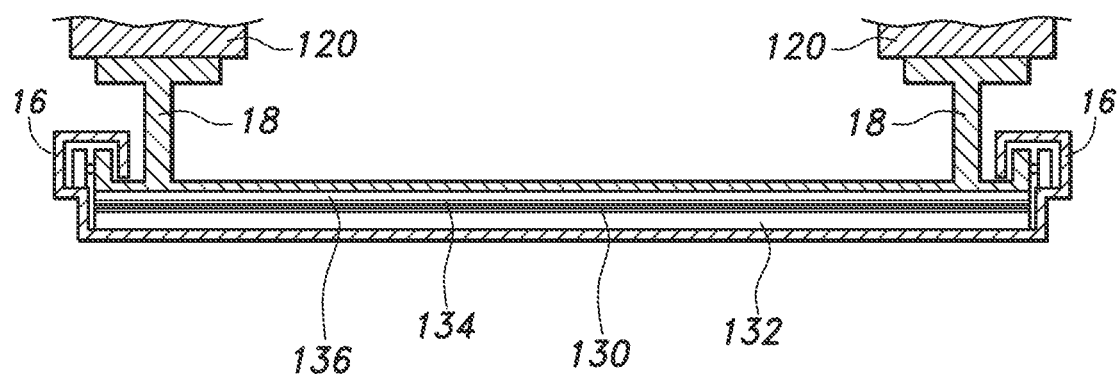
FIG. 11 is a cross-sectional view showing a main portion of a power supply mechanism of a seat device according to still another embodiment.

FIG. 11 shows a power supply mechanism according to still another embodiment. In this embodiment, the power transmitting electrode 130 and the power receiving electrode 134 extend between the left and right lower rails 16. Accordingly, the opposed areas of the power transmitting electrode 130 and the power receiving electrode 134 increase, and thus the transmittable electric power increases.

Incidentally, in this embodiment, the power transmitting electrode 130 and the power receiving electrode 134 may have uneven surfaces that are opposed to each other, like the embodiment shown in FIG. 10.

Figure 12:
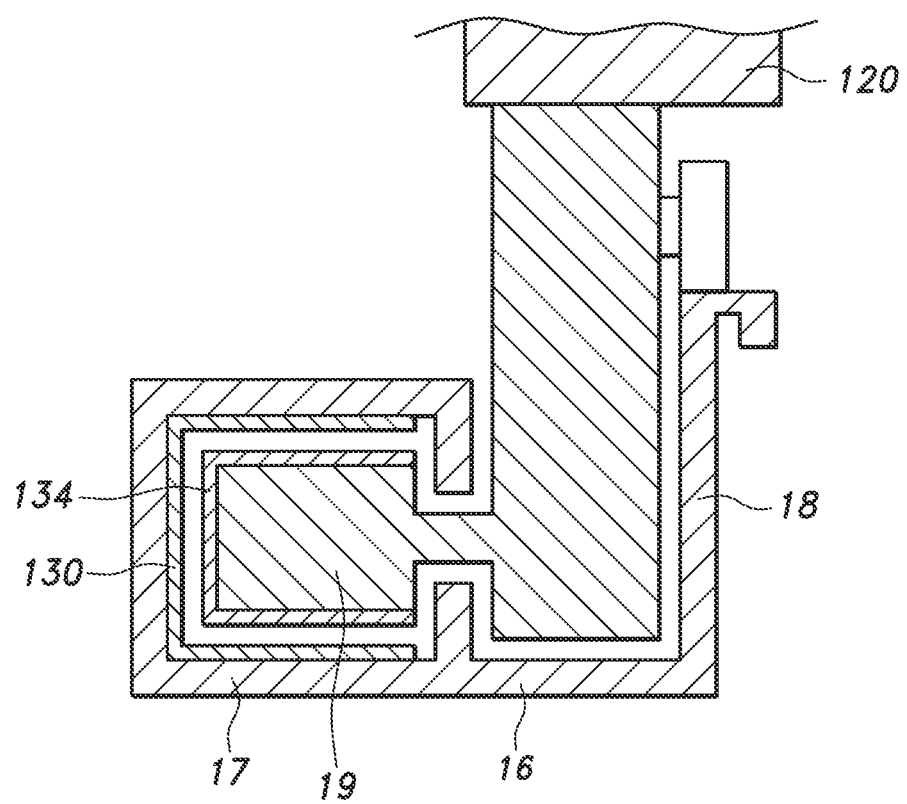
FIG. 12 is an enlarged cross-sectional view showing a main portion of a power supply mechanism of a seat device according to still another embodiment.

FIG. 12 shows a power supply mechanism according to still another embodiment. In this embodiment, the lower rail 16 has a box-shaped section 17. The power transmitting electrode 130 is provided on an inner surface of the box-shaped section 17. The upper rail 18 includes a slider 19 that enters the box-shaped section 17 from the inside. The power receiving electrode 134 is provided on an outer surface of the slider 19. In this embodiment, the power transmitting electrode 130 is not exposed to the outside.

Figure 13:
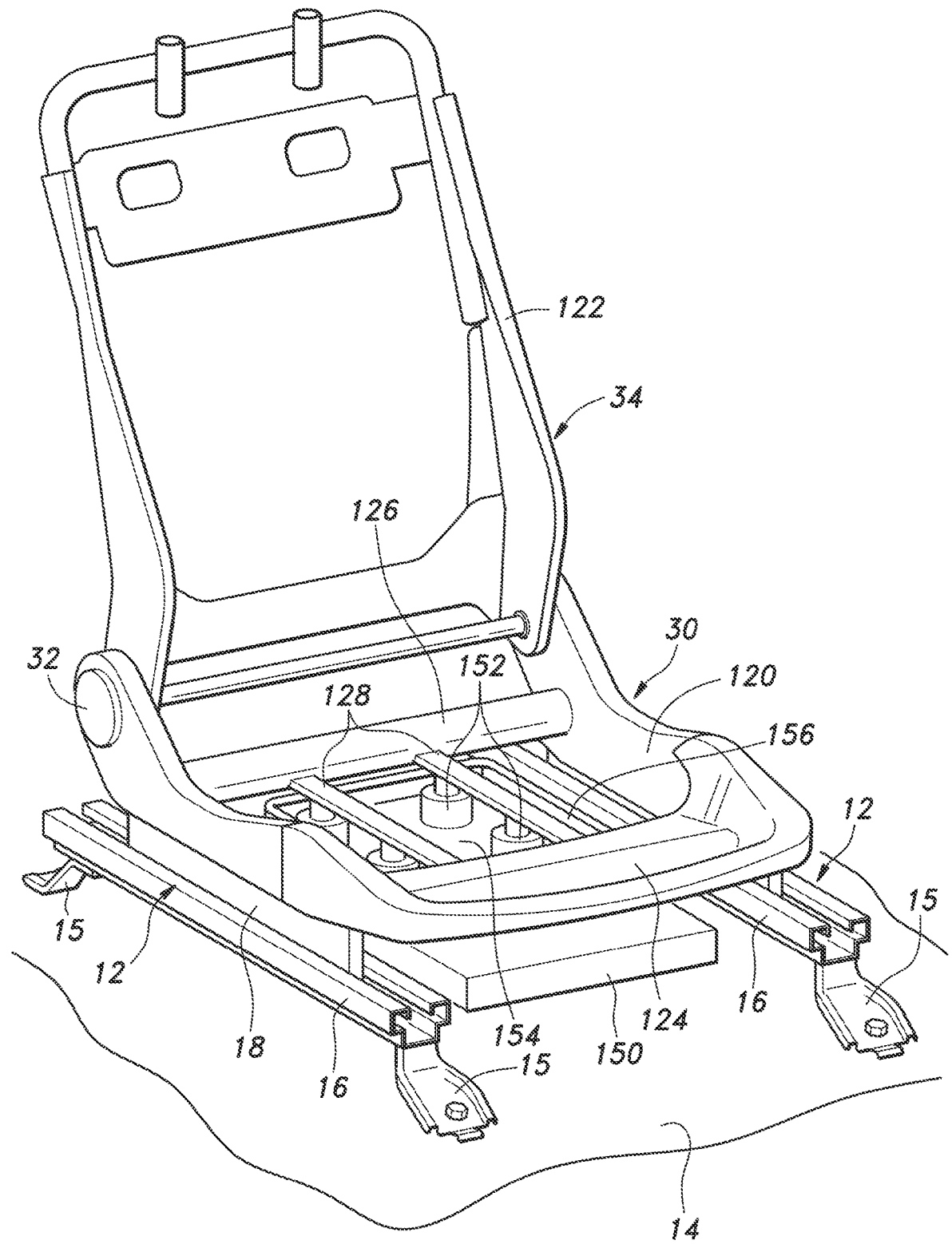
FIG. 13 is a perspective view showing a structure of a seat device according to still another embodiment.
Figure 14:
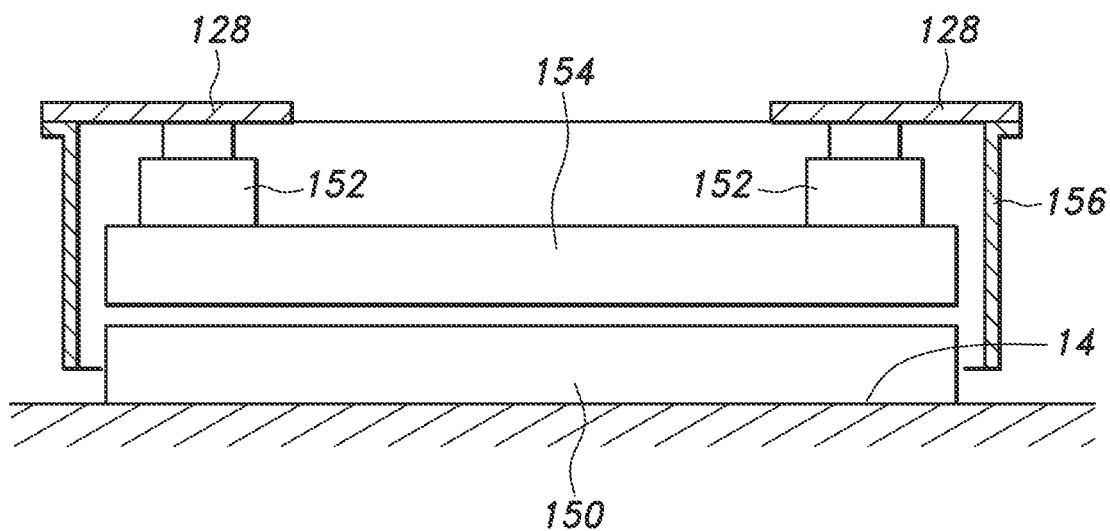
FIG. 14 is a cross-sectional view showing a main portion of a power supply mechanism in a seat device according to still another embodiment.

Next, a power supply mechanism according to still another embodiment will be described with reference to FIGS. 13 and 14. The power supply mechanism supplies the electric power from a power supply (not shown) on a vehicle body side to each portion of the seat device 10.

A power transmitter 150 is attached to the floor panel 14 between the left and right lower rails 16. Beams 128 extending in the front-and-rear direction is attached to a front member 124 and a rear member 126 of the seat cushion frame 120. A power receiver 154 is suspended from and supported by the beams 128 via dampers 152.

The power transmitter 150 and the power receiver 154 are opposed to each other with a prescribed gap therebetween, and compose a non-contact type power supply mechanism using magnetic field resonance. Accordingly, the electric power is supplied from the power supply (not shown) on the vehicle body side to each portion of the seat device 10.

A magnetic shield member 156 is attached to the beams 128 so as to surround the power receiver 154.

In this embodiment, the dampers 152 suppress the transmission of vibration from the side of the seat cushion frame 120 to the power receiver 154.

Figure 15:
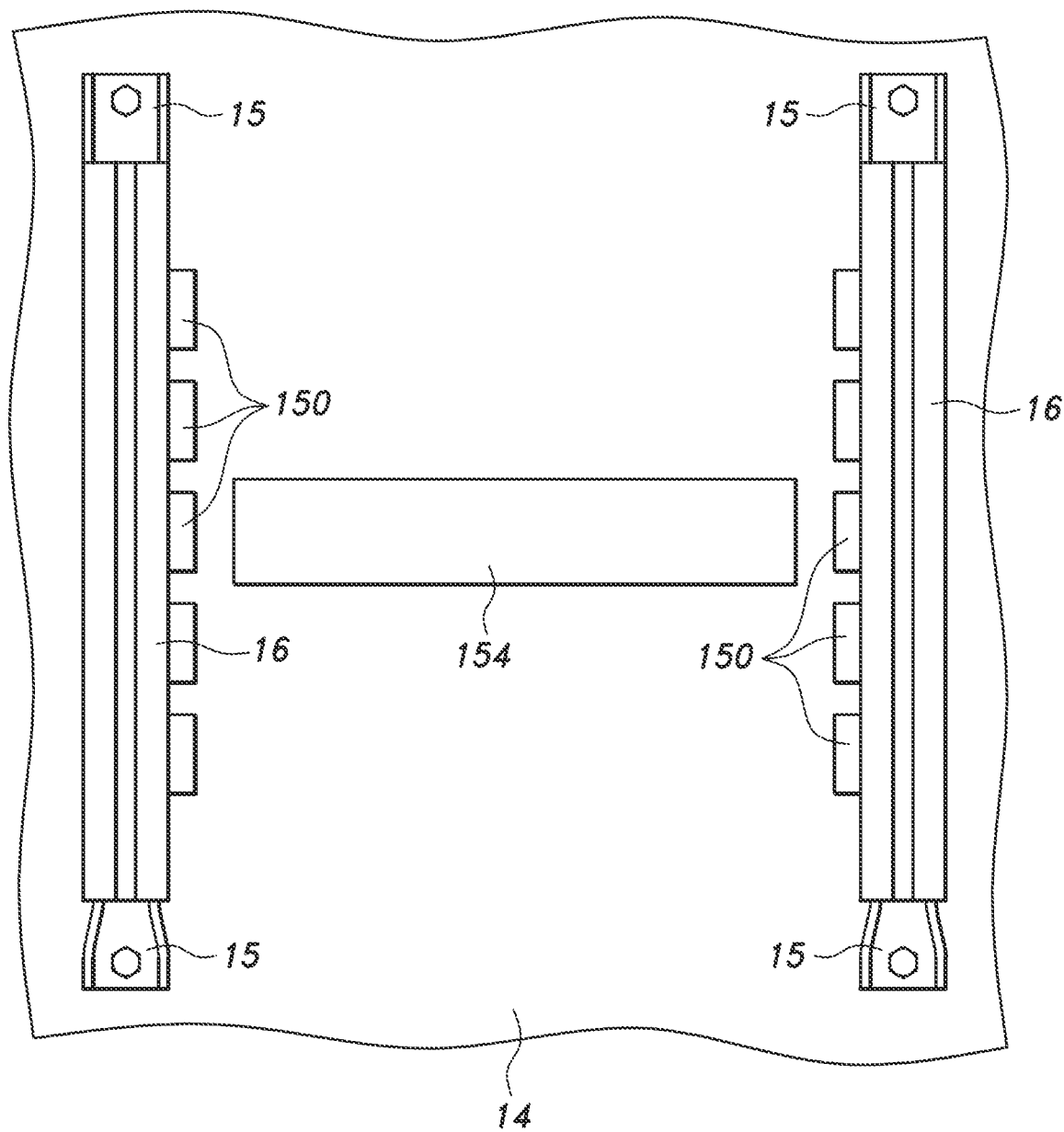
FIG. 15 is a plan view showing a main portion of a power supply mechanism of a seat device according to still another embodiment.

FIG. 15 shows a power supply mechanism using the magnetic field resonance according to still another embodiment. On inner surfaces of the left and right lower rails 16, a plurality of power transmitters 150 is provided at prescribed intervals along an extending direction of the lower rails 16.

Preferable embodiments of the present invention have been described in the foregoing. However, as easily understood by a skilled person, the present invention should not be limited by the foregoing embodiments, and various modifications and alterations are possible within the scope of the present invention. For example, the back pressing device 40, the waist pressing device 42, and the seat shape adjusting device 44 are not limited to an air pad, and may consist of a mechanical device using an electrostriction element that is deformed by the electric power, a cam, or the like. The exercise may not be realized by the seat shape adjusting device 44 but by a known electric lumbar support device installed in the seat back 34.

Also, not all components shown in the foregoing embodiment are necessarily indispensable, and they may be selectively used as appropriate within the scope of the present invention.

Glossary of Terms

10: seat device
12: slide rail device
14: floor panel
15: bracket
16: lower rail
17: box-shaped section
18: upper rail
19: slider
20: side door
22: window pane
30: seat cushion
32: electric reclining device
34: seat back
36: headrest
38: electric ottoman
40: back pressing device
42: waist pressing device
44: seat shape adjusting device (shape adjusting device)
46: body pressure detecting device
48: neck massaging device
50: calf massaging device
52: seat temperature adjusting device (temperature adjusting device)
56: knee back heater
58: warm air device
60: blanket box
62: blanket
64: locking hole
66: engagement hook
70: operation panel
72: breathing detecting device
74: heartbeat detecting device
76: cabin temperature/humidity detecting device
78: camera
90: cabin temperature/humidity adjusting device
92: cabin sound device
94: cabin lighting device
96: window shade device
98: display device
100: controller
102: sleep-inducing breathing control unit
104: sleeping level calculating unit
106: breathing control unit
108: seat temperature control unit 110: cabin environment control unit
112: massage control unit
114: posture control unit
116: reclining control unit
118: exercise control unit
120: seat cushion frame
122: seat back frame
124: front member
126: rear member
128: beam
130: power transmitting electrode
132: power transmitter
134: power receiving electrode
136: power receiver
138: bellows
150: power transmitter
152: damper
154: power receiver
156: magnetic shield member

The invention claimed is:

1. A seat device, comprising:
a seat body including a seat cushion and a seat back;
a pressing device provided in the seat back and configured to press a back or a waist of a seated person so as to induce breathing thereof;
shape adjusting devices configured to change a surface shape of the seat back; and
a controller configured to control the pressing device such that the pressing device presses the back or the waist of the seated person at a set cycle corresponding to a breathing cycle of a person at a sleeping time, and control the shape adjusting devices,
wherein the controller is configured to determine whether the breathing of the seated person is abdominal breathing or thoracic breathing, and control the pressing device so as to induce the abdominal breathing or the thoracic breathing corresponding to a determination result of whether the breathing of the seated person is the abdominal breathing or the thoracic breathing,
wherein the pressing device includes:
a back pressing device configured to press the back of the seated person so as to induce the thoracic breathing; and
a waist pressing device configured to press the waist of the seated person to induce the abdominal breathing, and
wherein the controller is configured to
cause the waist pressing device to operate so as to induce the abdominal breathing when sleep is induced, and
cause the back pressing device to operate so as to induce the thoracic breathing when the sleep ends,
wherein the waist pressing device is arranged below the back pressing device, and
the shape adjusting devices are provided in the seat back, arranged between the waist pressing device and the back pressing device, and spaced away from each other in a lateral direction,
wherein the seat device further comprises a plurality of body pressure detecting devices provided in the seat back and configured to detect a body pressure of the seated person,
the plurality of body pressure detecting devices includes:
a plurality of first body pressure detecting devices arranged between the shape adjusting devices and the waist pressing device and spaced away from each other in the lateral direction; and
a plurality of second body pressure detecting devices arranged below the waist pressing device and spaced away from each other in the lateral direction, and
each of the shape adjusting devices, each of the first body pressure detecting devices, and each of the second body pressure detecting devices are aligned in an up-and-down direction.

2. The seat device according to claim 1, wherein the controller is configured to correct the set cycle upon learning the breathing cycle of the seated person at the sleeping time.

3. The seat device according to claim 1, further comprising a breathing detecting device configured to detect the breathing of the seated person,
wherein in a case where the breathing detected by the breathing detecting device is unstable, the controller controls the pressing device so as to induce the breathing that eliminates unstableness in the breathing.

4. The seat device according to claim 1, further comprising a warm air device configured to warm feet of the seated person,
wherein the controller is configured to determine based on external information whether the seated person is likely to sleep, and perform control to turn on the pressing device and the warm air device upon determining that the seated person is likely to sleep.

5. The seat device according to claim 1, wherein the controller is configured to determine, based on external information, whether the seated person is likely to sleep, and turn on the pressing device and control the shape adjusting devices such that a massage synchronized with a breathing rhythm of the seated person is given upon determining that the seated person is likely to sleep.

6. The seat device according to claim 1, wherein the controller is configured to control the shape adjusting devices such that a massage synchronized with a breathing rhythm of the seated person is given.

7. The seat device according to claim 1,
wherein the controller is configured to control the shape adjusting devices such that a difference in the body pressure in each portion is reduced.

8. The seat device according to claim 1, wherein the controller is configured to control the shape adjusting devices such that surfaces of the seat cushion and the seat back are deformed so as to prompt the seated person to change a posture.

9. The seat device according to claim 1, wherein the controller is configured to control the shape adjusting devices such that surfaces of the seat cushion and the seat back are deformed at a set wake-up time so as to promote the seated person to wake up.

10. The seat device according to claim 1, wherein the seat device is for a vehicle.

11. The seat device according to claim 1, wherein the seat device is for an automobile configured to be driven autonomously.

12. The seat device according to claim 1, wherein the controller is configured to cause only one of the back pressing device and the waist pressing device to operate so as to induce the breathing corresponding to the determination result thereof.

13. The seat device according to claim 1, wherein the controller includes a posture control unit configured to control the shape adjusting devices.

14. The seat device according to claim 13, wherein in a sleep-inducing mode for inducing sleep of the seated person, the posture control unit controls the shape adjusting devices based on distribution of the body pressure detected by each of the body pressure detecting devices so as to correct the distribution of the body pressure, prevent a bedsore, or prompt the seated person to roll over.

15. The seat device according to claim 13, wherein the seat device is provided in an automobile, and
in a case where the seated person sleeps while the automobile is traveling, the posture control unit performs control such that the shape adjusting devices cause the seat cushion and the seat back to hold the seated person tight or harden the seat cushion and the seat back according to a travel acceleration.

16. A seat device, comprising:
a seat body including a seat cushion and a seat back;
a pressing device provided in the seat back and configured to press a back or a waist of a seated person so as to induce breathing thereof;
shape adjusting devices configured to change a surface shape of the seat back; and
a controller configured to control the pressing device such that the pressing device presses the back or the waist of the seated person at a set cycle corresponding to a breathing cycle of a person at a sleeping time, and control the shape adjusting devices,
wherein the controller is configured to control the pressing device so as to induce abdominal breathing when sleep is induced, and induce thoracic breathing when the sleep ends,
wherein the pressing device includes:
a back pressing device configured to press the back of the seated person so as to induce the thoracic breathing; and
a waist pressing device configured to press the waist of the seated person to induce the abdominal breathing, and
wherein the controller is configured to
cause the waist pressing device to operate so as to induce the abdominal breathing when the sleep is induced, and
cause the back pressing device to operate so as to induce the thoracic breathing when the sleep ends,
wherein the waist pressing device is arranged below the back pressing device, and
the shape adjusting devices are provided in the seat back, arranged between the waist pressing device and the back pressing device, and spaced away from each other in a lateral direction,
wherein the seat device further comprises a plurality of body pressure detecting devices provided in the seat back and configured to detect a body pressure of the seated person,
the plurality of body pressure detecting devices includes:
a plurality of first body pressure detecting devices arranged between the shape adjusting devices and the waist pressing device and spaced away from each other in the lateral direction; and
a plurality of second body pressure detecting devices arranged below the waist pressing device and spaced away from each other in the lateral direction, and
each of the shape adjusting devices, each of the first body pressure detecting devices, and each of the second body pressure detecting devices are aligned in an up-and-down direction.

17. The seat device according to claim 16, wherein the controller includes a posture control unit configured to control the shape adjusting devices.

18. The seat device according to claim 17, wherein in a sleep-inducing mode for inducing sleep of the seated person, the posture control unit controls the shape adjusting devices based on distribution of the body pressure detected by each of the body pressure detecting devices so as to correct the distribution of the body pressure, prevent a bedsore, or prompt the seated person to roll over.

19. The seat device according to claim 18, wherein the seat device is provided in an automobile, and
in a case where the seated person sleeps while the automobile is traveling, the posture control unit performs control such that the shape adjusting devices cause the seat cushion and the seat back to hold the seated person tight or harden the seat cushion and the seat back according to a travel acceleration.

\* \* \* \* \*